United States Patent [19]
Bollinger et al.

[11] Patent Number: 5,525,590
[45] Date of Patent: Jun. 11, 1996

[54] CYCLOSPORINS AND THEIR USE AS PHARMACEUTICALS

[75] Inventors: Pietro Bollinger, Bottmingen; Johann J. Bölsterli, Buus; Trevor G. Payne, Bern; all of Switzerland

[73] Assignee: Sandoz Ltd., Basel, Switzerland

[21] Appl. No.: 337,346

[22] Filed: Nov. 10, 1994

Related U.S. Application Data

[63] Continuation of Ser. No. 67,274, May 24, 1993, abandoned, which is a continuation of Ser. No. 874,676, Apr. 27, 1992, abandoned, which is a continuation of Ser. No. 704,758, May 23, 1991, abandoned, which is a continuation of Ser. No. 208,422, Jun. 17, 1988, abandoned.

[30] Foreign Application Priority Data

| Jun. 17, 1987 | [GB] | United Kingdom | 8714090 |
|---|---|---|---|
| Jun. 17, 1987 | [GB] | United Kingdom | 8714093 |
| Jun. 17, 1987 | [GB] | United Kingdom | 8714098 |
| Jun. 17, 1987 | [GB] | United Kingdom | 8714100 |
| Jun. 17, 1987 | [GB] | United Kingdom | 8714115 |
| Jun. 17, 1987 | [GB] | United Kingdom | 8714118 |
| Jun. 17, 1987 | [GB] | United Kingdom | 8714119 |
| Jun. 17, 1987 | [GB] | United Kingdom | 8714125 |

[51] Int. Cl.$^6$ .............................. A61K 38/13; C07K 7/64
[52] U.S. Cl. ................................ 514/11; 530/321
[58] Field of Search ................................ 530/321; 514/11

[56] References Cited

U.S. PATENT DOCUMENTS

| 4,108,985 | 8/1978 | Rüegger et al. | 530/321 |
|---|---|---|---|
| 4,210,581 | 7/1980 | Rüegger et al. | 530/321 |
| 4,798,823 | 1/1989 | Witzel | 514/11 |

OTHER PUBLICATIONS

Durette et al., Transplant Proc. 20 suppl. 2 (Book I) CYA 5947, pp. 51–57 (1988).
Rudinger, Peptide Hormones, Parsons (Ed.), U Park Press, Baltimore, pp. 1–7 (1976).
Tetrahedron Letters, vol. 30, No. 32, pp. 4215–4218, 1989.
Anticancer Research 8: 985–994 (1988).
Int. J. Cancer: 41, 462–467 (1988).
Progress in Clinical Biochemistry & Medicine, vol. 3—Springer–Verlag Berlin Heidelberg 1986, 157–191.
Cancer Chemother Pharmacol (1986) 18: 198–202.
Br.J.Cancer (1987) 56, 55–57.
Brit.J.Cancer 54, 235–238 (1986).
J.Clin.Invest. vol. 77, Apr. 1986, 1405–1408.
Klin.Wschr. 63, 1081–1082 (1985).
Proceedings of AACR vol. 28 Mar. 1987—298.
Br.J.Cancer (1988), 57, 254–258.
Progress in the Chemistry of Organic Natural Products—Wien–Springer–Verlag–NY (1986), 123–168.
Science—2 Nov. 1984—vol. 226—No. 4674—544–546.
Poster—EMBO Symposium, Heidelberg, BRD, May 1986.

*Primary Examiner*—Jeffrey E. Russel
*Attorney, Agent, or Firm*—Robert S. Honor; Melvyn M. Kassenoff; Thomas O. McGovern

[57] ABSTRACT

Cyclosporins wherein the residue at the 1-position (typically -MeBmt- or -dihydro-McBmt-) is 3'O-acylated or 3'-oxo or -$C_{1-4}$alkoxyimino substituted, or wherein the residue at the 2-position is β-O-acyl or β-oxo substituted, or wherein the residue at the 2-position is -Ile-, or wherein the residue at the 11-position is -MeAls-, -MeIle- or -Meallolle- as well as various naturally occurring cyclosporins/dihydro-derivatives thereof, are useful in reversing resistance to chemotherapy, in particular resistance to cytostatic or anti-neoplastic therapy. Various of these cyclosporins and intermediates for their production are novel. Intermediates wherein the residue (e.g. -MeBmt-, -dihydro-MeBmt- etc.) at the 1-position is 8'-alkoxy or 7'-desmethyl-7'-hydrocarbyl substituted are novel and useful as immunosuppressants, anti-inflammatory and anti-parasitic agents.

5 Claims, No Drawings

CYCLOSPORINS AND THEIR USE AS PHARMACEUTICALS

This is a continuation of application Ser. No. 08/067/274, filed May 24, 1993 and now abandoned, which is a continuation of application Ser. No. 07/874,676, filed Apr. 27, 1992, which in turn is a continuation of application Ser. No. 07/704,758, filed May 23, 1991 which in turn is a continuation of application Ser. No. 07/208,422, filed Jun. 17, 1988, the latter three of which are now abandoned.

The present invention relates to a new use, in particular a new pharmaceutical use, for cyclosporins, as well as to new cyclosporins as novel compounds per se.

The cyclosporins comprise a class of structurally distinctive, cyclic, poly-N-methylated undecapeptides, generally possessing pharmacological, in particular immunosuppressive, anti-inflammatory and/or anti-parasitic activity, each to a greater or lesser degree. The first of the cyclosporins to be isolated was the naturally occurring fungal metabolite Ciclosporin or Cyclosporine, also known as cyclosporin A and now commercially available under the registered trademark SANDIMMUN®. Ciclosporin is the cyclosporin of formula A

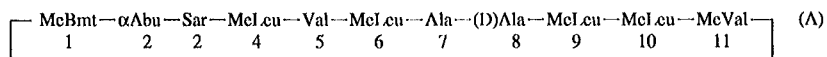

wherein -McBmt- represents the N-methyl-(4R)-4-but-2E-en-1-yl-4-methyl-(L)threonyl residue of formula B

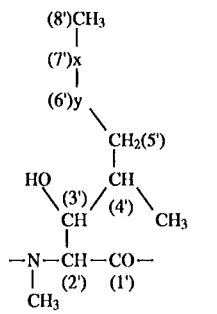

in which —x—y— is trans —CH=CH— and the position 2', 3' and 4' have the configuration S, R and R respectively.

Since the original discovery of Ciclosporin, a wide variety of naturally occurring cyclosporins have been isolated and identified and many further non-natural cyclosporins have been prepared by total- or semi-synthetic means or by the application of modified culture techniques. The class comprised by the cyclosporins is thus now substantial and includes, for example, the naturally occurring cyclosporins A through Z [c.f. Traber et al. 1, Helv. Chim. Acta, 60, 1247–1255 (1977); Traber et al. 2, Helv. Chim. Acta, 65, 1655–1667 (1982); Kobel et al., Europ. J. Applied Microbiology and Biotechnology 14, 237–240 (1982); and von Wartburg et al., Progress in Allergy, 38, 28–45 (1986)], as well as various non-natural cyclosporin derivatives and artificial or synthetic cyclosporins including the dihydro- and iso-cyclosporins [in which the moiety —x—y— of the -McBmt- residue (Formula B above) is saturated to give —x—y—=—$CH_2$—$CH_2$—/the linkage of the residue -McBmt- to the residue at the 11-position of the cyclosporin molecule (Formula A above) is via the 3'-O-atom rather than the α-N-atom]; derivatised cyclosporins (e.g. in which the 3'-O-atom of the -McBmt- residue is acylated or a further substituent is introduced at the α-carbon atom of the sarcosyl residue at the 3-position); cyclosporins in which the -McBmt- residue is present in isomeric form (e.g. in which the configuration across positions 6' and 7' of the -McBmt- residue is cis rather than trans); and cyclosporins wherein variant amino acids are incorporated at specific positions within the peptide sequence employing e.g. the total synthetic method for the production of cyclosporins developed by R. Wenger—see e.g. Traber et al. 1, Traber et al. 2 and Kobel et al. loc. cit.; U.S. Pat. Nos. 4,108,985, 4,210,581, 4,220,641, 4,288,431, 4,554,351 and 4,396,542; European Patent Publications Nos. 0 034 567 and 0 056 782; International Patent Publication No. WO 86/02080; Wenger 1, Transpl. Proc. 15, Suppl. 1:2230 (1983); Wenger 2, Angew. Chem. Int. Ed., 24, 77 (1985); and Wenger 3, Progress in the Chemistry of Organic Natural Products 50, 123 (1986).

The class comprised by the cyclosporins is thus now very large indeed and includes, for example, [Thr]²-, [Val]²-, [Nva]²- and [Nva]²-[Nva]⁵-Ciclosporin (also known as cyclosporins C, D, G and M respectively), [3-O-acetyl-McBmt]¹-Ciclosporin (also known as cyclosporin A acetate), [Dihydro-McBmt]¹-[Val]²-Ciclosporin (also known as dihydro-cyclosporin D), [Iso-McBmt]¹-[Nva]²-Ciclosporin (also known as isocyclosporin G), [(D)Ser]⁸-Ciclosporin, [MeIle]¹¹-Ciclosporin, [(D)MeVal]¹¹-Ciclosporin (also known as cyclosporin H), [McAla]⁶-Ciclosporin, [(D)Pro]³-Ciclosporin and so on.

[In accordance with conventional nomenclature for cyclosporins, these are defined throughout the present specification and claims by reference to the structure of Ciclosporin (i.e. Cyclosporin A). This is done by first indicating the amino acid residues present which differ from those present in Ciclosporin (e.g. "[(D)Pro]³" to indicate that the cyclosporin in question has a -(D)Pro- rather than -Sar- residue at the 3-position) and then applying the term "Ciclosporin" to characterise remaining residues which are identical to those present in Ciclosporin.

The residue -McBmt- at position 1 in Ciclosporin was unknown before the discovery of the cyclosporins. This residue and variants or modifications of it, e.g. as described below, are thus generally characteristic of the cyclosporins. In general, variants or alternatives to [McBmt]¹ are defined by reference to the -McBmt- structure. Thus for dihydrocyclosporins in which the moiety —x—y— (see formula B above) is reduced to —$CH_2$—$CH_2$—, the residue at the 1-position is defined as "-dihydro-McBmt-". Where the configuration across the moiety —x—y— is cis rather than trans, the resulting residue is defined as "-cis-McBmt-".

Where portions of the -McBmt- residue are deleted, this is indicated by defining the position of the deletion, employing the qualifier "des" to indicate deletion, and then defining the group or atom omitted, prior to the determinant "-McBmt-", "-dihydro-McBmt-", "-cis-McBmt-" etc. Thus "-N-desmethyl-McBmt-", "-3'-desoxy-McBmt-" and "-3'-desoxy-4'-desmethyl-McBmt-" are the residues of Formula B¹, B², and B³ respectively:

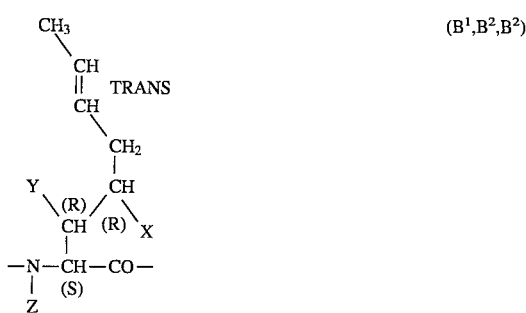

$B^1$—X=CH$_3$, Y=OH, Z=H.
$B^2$—X=CH$_3$, Y=H, Z=CH$_3$.
$B^3$—X=H, Y=H, Z=CH$_3$.

Where positions or groups, e.g. in -MeBmt-, are substituted, this is represented in conventional manner by defining the position and nature of the substitution. Thus -3'-O-acetyl-MeBmt- is the residue of formula B in which the 3'-OH group is acetylated (3'-O—COCH$_3$). Where substituents or groups, in e.g. -MeBmt-, are replaced, this is done by i) indicating the position of the replaced group by "des- terminology" as described above and ii) defining the replacing group. Thus -7'-desmethyl-7'-phenyl-MeBmt- is the residue of formula B above in which the terminal (8') methyl group is replaced by phenyl. 3'-Desoxy-3'-oxo-MeBmt- is the residue of formula B above in which the 3'-OH group is replaced by =O.

In addition, amino acid residues referred to by abbreviation, e.g. -Ala-, -MeVal- and -αAbu-, are, in accordance with conventional practice, to be understood as having the (L)-configuration unless otherwise indicated, e.g. as in the case of "-(D)Ala-". Residue abbreviations preceded by "Me" as in the case of "-MeLeu-", represent α-N-methylated residues. Individual residues of the cyclosporin molecule are numbered, as in the art, clockwise and starting with the residue -MeBmt-, -dihydro-MeBmt- etc. . . . in position 1. The same numerical sequence is employed throughout the present specification and claims.

Because of their unique pharmaceutical potential, the cyclosporins have attracted very considerable attention, not only in medical and academic circles, but also in the lay press. Cyclosporin itself is now commonly employed in the prevention of rejection following allogenic organ, e.g. heart, heart-lung, kidney and bone-marrow transplant, as well as, more recently, in the treatment of various auto-immune and related diseases and conditions. Extensive work has also been performed to investigate potential utility in the treatment of various parasitic diseases and infections, for example coccidiomycosis, malaria and schistosomiasis. Reports of investigative work into the potential utility of the very many other known cyclosporins in these or related indications now abound in the literature.

In accordance with the present invention it has now surprisingly been found that particular cyclosporins are useful in increasing sensitivity to other chemotherapy and, in particular, of affecting reversal of resistance, whether induced or inherent, to other chemotherapy.

Increased resistance to chemotherapeutic therapy following treatment over shorter or longer periods of time, generally following relatively prolonged chemotherapeutic medication, is a wide-spread phenomenon which has long been recognised and is widely documented in the art. The classic example is the increased or induced resistance of parasitic, in particular bacterial, viral or protozoal, organisms, following long-term or wide-spread medication employing individual drug-substances. In such instances the infecting organism becomes, with time, resistant to the drug substance to a greater or lesser degree and concomitantly difficult to combat or treat. An analogous phenomenon is observed in relation to the chemotherapeutic treatment of cancers, e.g. treatment of carcinomas, sarcomas or other tumors or malignant growths.

Chemotherapeutic treatment of cancers, e.g. by administration of drug substances, in particular anti-neoplastic or cytotoxic drugs, for example colchicine, etoposide, tenoposide, adriamycin, daunorubicin and vincristine, as a means of reducing, inhibiting or otherwise limiting tumor growth or metastasis, remains a first line approach to the treatment of cancers of various type. However it is commonly found that, while tumors may be susceptible to therapy initially, as treatment continues, resistance to such therapy develops, resulting in a decline in therapeutic efficacy. Where, as is common, in particular in the treatment of late-phase or terminal cancers, pleiotropic or multi-drug therapy is employed, multi-drug resistance commonly ensues. Analogous difficulties arise, e.g. in cases where particular forms of chemotherapeutic treatment have long been practiced and, for example, resistant strains of micro-organism arise which have developed an inherent or innate resistance. So too, particular forms of cancer or tumor are frequently encountered which exhibit an innate resistance to, or reduced level of sensitivity to, commonly employed anti-neoplastic or cytostatic drug therapy.

In accordance with the present invention it has been found that the cyclosporins hereinafter defined are useful in increasing sensitivity to, or increasing the efficacy of, chemotherapeutic drug therapy and, in particular, are useful in reversing chemotherapeutic drug resistance of varying types (e.g. acquired or innate), or in increasing or restoring sensitivity to administered drug therapy. Forms of chemotherapeutic drug therapy to which the present invention is applicable include, for example, anti-parasitic, e.g. anti-viral, anti-bacterial or anti-protozoal chemotherapy and, in particular, anti-neoplastic or cytostatic chemotherapy.

Cyclosporins suitable for use in accordance with the present invention are definable under various classes as follows.

Class 1

A cyclosporin wherein the 3'-carbon atom of the residue at the 1-position or the β-carbon atom of the residue at the 2-position is O-acyl or oxo substituted.

Preferred cyclosporins of this class are those:

1a) Wherein the 3'-carbon atom of the residue at the 1-position is O-acyl substituted.

When the 3'-carbon atom of the residue at the 1-position is O-acyl substituted, the residue at the 2-position may also be β-O-acylated.

A preferred group of cyclosporins of type 1a) are those:

1a$^1$) Wherein the residue at the 1-position is a -3'-O-acyl-MEBmt- or -3'-O-acyl-dihydro-MeBmt- residue of formula I

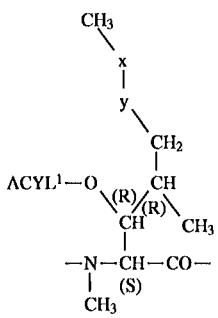

(I)

wherein —x—y— is —CH₂—CH₂— or trans —CH=CH— and ACYL¹ represents an acyl group.

Suitable acyl groups as ACYL¹ in formula I, are those of formula $R_1$—CO— and $R_2$—O—CO— wherein $R_1$ is $C_{1-4}$alkyl or $C_{1-4}$azidoalkyl and $R_2$ is $C_{1-4}$alkyl, e.g. acetyl, 4-azidobutanoyl or methoxycarbonyl. Preferably ACYL¹ is a group of formula $R_1$—CO—, in which case $R_1$ is preferably $C_{1-4}$alkyl. Most preferably $R_1$—CO— is acetyl.

Alkyl groups as or comprising $R_1$ and $R_2$ may be branched or straight chain. Preferably they are straight chain. $R_1$ is most preferably methyl.

Especially preferred cyclosporins of group 1a¹ are those of the formula II or II'

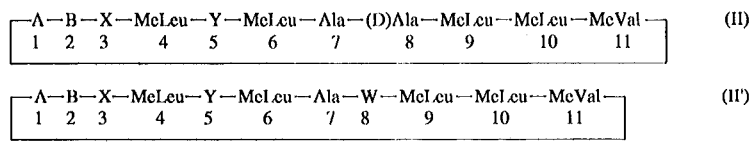

wherein

A is a residue as defined under 1a¹ above

B is -αAbu-, -Thr-, -Val-, -Nva- or the residue of a β-O-acyl-α-amino acid,

X is -Sar- or the residue of an optically active, α-N-methylated α-amino acid residue having the (D)-configuration, Y is -Val- or additionally, when B is -Nva-, -Nva-, and W is the residue of a β-hydroxy- or β-O-acyl-α-amino acid having the (D)-configuration.

When B is a β-O-acyl-α-amino acid residue, this will generally have the (L) configuration. Suitably it is a residue of formula III

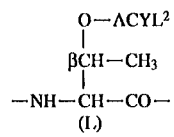

Wherein ACYL² represents an acyl group. Preferably it is an O-acyl-(L)-threonyl residue.

W is suitably -(D)Ser- or -(D)Thr- or O-acyl-(D)Ser- or O-acyl-(D)Thr- of formula III'

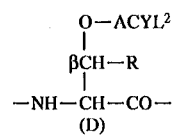

Wherein ACYL² has the meaning given for formula III and R is hydrogen or methyl.

Preferred acyl groups as ACYL² in formula III and III' are those of the formula $R_3$—CO— wherein $R_3$ is $C_{1-4}$alkyl.

Alkyl groups as $R_3$ may be branched or straight chain. Preferably they are straight chain. Suitably ACYL² is acetyl.

When X in formula II is other than -Sar-, it is suitably -(D)Ala-.

Examples of cyclosporins of this class suitable for use in accordance with the present invention are:

1.1 [3'-O-Acetyl-McBmt]¹-Ciclosporin;
1.2 [3'-O-Acetyl-McBmt]¹-[Val]²-Ciclosporin;
1.3 [3'-O-Acetyl-McBmt]¹-[Thr]²-Ciclosporin;
1.4 [3'-O-Acetyl-McBmt]¹-[Nva]²-Ciclosporin;
1.5 [3'-O-Acetyl-McBmt]¹-[Nva]²-[Nva]⁵-Ciclosporin;
1.6 [3'-O-Acetyl-McBmt]¹-[(D)Ala]³-Ciclosporin;
1.7 [3'-O-Acetyl-McBmt]¹-[Nva]²-[(D)Ala]³-Ciclosporin;
1.8 [3'-O-Acetyl-McBmt]¹-[(D)McVal]¹¹-Ciclosporin;
1.9 [3'-O-Acetyl-McBmt]¹-[Val]¹¹-Ciclosporin;
1.10 [3'-O-Acetyl-dihydro-McBmt]¹-Ciclosporin;
1.11 [3'-O-Methoxycarbonyl-McBmt]¹-Ciclosporin;
1.12 [3'-O-(4-Azidobutanoyl)-McBmt]¹-Ciclosporin;
1.13 [3'-O-Acetyl-McBmt]¹-[O-acetyl-Thr]²-Ciclosporin;
1.14 [3'-O-Acetyl-N-desmethyl-McBmt]¹-[O-acetyl-Thr]²-Ciclosporin; and
1.15 [3'-O-Acetyl-McBmt]¹-[O-acetyl-(D)Ser]⁸-Ciclosporin;

Preferred cyclosporins for use in accordance with the invention are cyclosporins 1.1 to 1.10 inclusive and 1.15 above and, most especially, cyclosporins 1.1, 1.2, 1.3, 1.4, 1.10 and 1.15.

A further group of cyclosporins of type 1a are those:

1a²) Wherein the residue at the 1-position is a -3'-O-acyl-8'-$C_{1-8}$-alkoxy- -cis-McBmt- or -dihydro-McBmt- residue of the formula IV

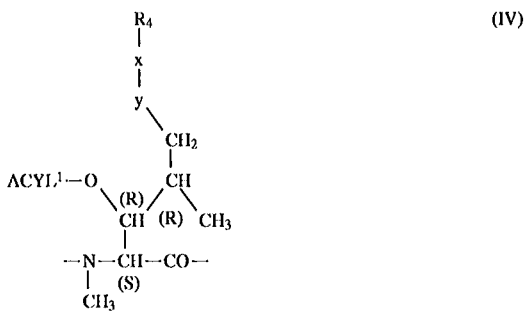

wherein

—x—y— is cis —CH=CH— or —CH₂—CH₂—, $R_4$ is $C_{2-9}$alkoxymethyl and ACYL¹ represents an acyl group.

Especially suitable as acyl groups in formula IV are those of formula $R_5$—CO— wherein $R_5$ is $C_{1-4}$alkyl.

Alkyl groups as $R_5$, as well as alkyl moieties comprising $R_4$, may be branched or straight chain. Preferably they are straight chain. Preferably $R_4$ is $C_{2-5}$alkoxymethyl. ACYL¹ in formula IV is suitably acetyl.

Especially preferred cyclosporins of group 1a² are those of formula II as illustrated above, wherein A is a residue of formula IV as defined above, B has the meanings given for formula II, X is -Sar- and Y is -Val-.

Examples of cyclosporins of group 1a², suitable for use in accordance with the present invention are:

1.16 [3'-O-acetyl-8'-methoxy-cis-McBmt]¹-Ciclosporin;

1.17 [3'-O-acetyl-8'-t.butoxy-cis-MeBmt]$^1$-Ciclosporin;
1.18 [3'-O-acetyl-8'-methoxy-cis-MeBmt]$^1$-[O-acetyl-Thr]$^2$-Ciclosporin;
1.19 [3'-O-acetyl-8'-t.butoxy-cis-MeBmt]$^1$-[O-acetyl-Thr]$^2$-Ciclosporin;
1.20 [3'-O-acetyl-8'-methoxy-cis-MeBmt]$^1$-[Val]$^2$-Ciclosporin; and
1.21 [3'-O-acetyl-8'-methoxy-cis-MeBmt]$^1$-[Nva]$^2$-Ciclosporin.

A further group of cyclosporins of type 1a are those:

1a$^3$) Wherein the residue at the 1-position is a -3'-O-acyl-cis-MeBmt-; a -3'-O-acyl-7'-desmethyl-7'-hydrocarbyl--MeBmt- or -cis-MeBmt- residue, wherein the hydrocarbyl moiety comprises at least two carbon atoms; or a -3'-O-acyl-7'-desmethyl-7'-hydrocarbyl-dihydro-MeBmt- residue, wherein the hydrocarbyl moiety comprises at least two carbon atoms and wherein any aliphatic group or moiety present in said hydrocarbyl moiety is saturated.

These residues may be represented by the formula V

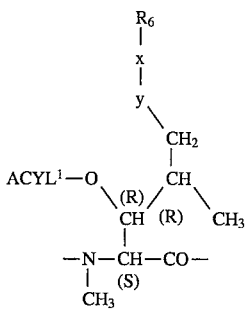

wherein

—x—y— is cis or trans —CH=CH— or —CH$_2$—CH$_2$—,

R$_6$ is hydrocarbyl and ACYL$^1$ represents an acyl group, with the proviso that, when —x—y— is trans —CH=CH— or —CH$_2$—CH$_2$—, R$_6$ comprises at least two carbon atoms (i.e. is other than methyl), and when —x—y— is —CH$_2$—CH$_2$— any aliphatic group or moiety present as or in R$_6$ is saturated.

Especially suitable as acyl groups in formula V are those of formula R$_5$—CO— wherein R$_5$ is C$_{1-4}$alkyl, in particular acetyl.

Hydrocarbyl groups as R$_6$ include aromatic, aliphatic and araliphatic groups, whereby aliphatic groups and moieties may be branched or straight chain. Such groups may also bear further substituents such as halogen or hydroxy or may be unsubstituted.

Suitable hydrocarbyl groups as R$_6$ are alkyl, alkenyl, alkinyl, phenyl, phenylalkyl, phenylalkenyl and phenylalkinyl, especially alkyl, alkenyl and alkinyl groups containing maximally 20, preferably maximally 8 carbon atoms, and phenyl, phenylalkyl and phenylalkinyl groups containing maximally 12 carbon atoms.

Especially preferred groups R$_6$ are phenyl, phenyl-(C$_{1-4}$alkyl), C$_{1-10}$-alkyl, C$_{2-10}$alkenyl and C$_{2-10}$alkinyl, especially phenyl, and C$_{1-5}$-alkyl.

When —x—y— in formula V is —CH$_2$—CH$_2$—, hydrocarbyl groups as R$_6$ will include aromatic, saturated aliphatic and araliphatic groups in which the aliphatic moiety is saturated, e.g. including any such groups of this type as set forth above.

Especially preferred cyclosporins of this group are those of formula II as illustrated above, wherein A is a residue of formula V as defined above, B has the meanings given for formula II, X is -Sar- and Y is -Val-.

Examples of cyclosporins of this group, suitable for use in accordance with the present invention are:

1.22 [3'-O-acetyl-7'-desmethyl-7'-phenyl-MeBmt]$^1$-Ciclosporin;
1.23 [3'-O-acetyl-cis-MeBmt]$^1$-Ciclosporin;
1.24 [3'-O-acetyl-7'-desmethyl-7'-vinyl-cis-MeBmt]$^1$-Ciclosporin;
1.25 [3'-O-acetyl-7'-desmethyl-7'-vinyl-cis-MeBmt]$^1$-[O-acetyl-Thr]$^2$-Ciclosporin;
1.26 [3'-O-acetyl-7'-desmethyl-7'-i.pentyl-cis-MeBmt]$^1$-Ciclosporin;
1.27 [3'-O-acetyl-7'-desmethyl-7'-phenyl-cis-MeBmt]$^1$-Ciclosporin;
1.28 [3'-O-acetyl-7'-desmethyl-7'-n.propyl-cis-MeBmt]$^1$-Ciclosporin;
1.29 [3'-O-acetyl-7'-desmethyl-7'-(β-allyl)-cis-MeBmt]$^1$-Ciclosporin;
1.30 [3'-O-acetyl-7'-desmethyl-7'-phenyl-MeBmt]$^1$-[Val]$^2$-Ciclosporin;
1.31 [3'-O-acetyl-7'-desmethyl-7'-phenyl-cis-MeBmt]$^1$-[Val]$^2$-Ciclosporin;
1.32 [3'-O-acetyl-7'-desmethyl-7'-vinyl-cis-MeBmt]$^1$-[Val]$^2$-Ciclosporin;
1.33 [3'-O-acetyl-7'-desmethyl-7'-vinyl-cis-MeBmt]$^1$-[Nva]$^2$-Ciclosporin; and
1.34 [3'-O-acetyl-7'-desmethyl-7'-(3-bromo-n.propyl)-cis-MeBmt]$^1$-Ciclosporin;

A further group of cyclosporins of CLASS 1 are those:

1b) Wherein the β-carbon atom of the residue at the 2-position is O-acyl substituted, i.e. wherein the residue at the 2-position is a β-O-acyl-α-amino acid residue, and the residue at the 1-position is other than as defined under 1a) above.

When the residue at the 2-position is a β-O-acyl-α-amino acid residue, this residue will generally have the (L) configuration. Suitably it is a residue of formula III"

in which ACYL$^3$ represents an acyl group. Preferably it is an O-acyl-(L)-threonyl residue.

Suitable groups as ACYL$^3$ in formula III", are those of the formula R$_3$—CO— or R$_7$—CO—R$_8$CO—, wherein R$_3$ has the meanings given for formula III, R$_7$ is the residue of a cyclosporin having a β-oxy-(L)-α-amino acid residue in the 2-position attached to the moiety —CO—R$_8$CO— via the β-oxygen atom of said residue, and R$_8$ is C$_{1-8}$-alkylene.

Alkylene groups as R$_8$ may be branched or straight chain. Preferably they are straight chain. R$_8$ is preferably C$_{1-4}$alkylene. Acyl groups of formula R$_3$—CO— are generally preferred, preferred significances for R$_3$—CO— being as hereinbefore set forth in relation to formula III.

Particular cyclosporins of this group are those of formula II as illustrated above, wherein A is -MeBmt- or -dihydro-MeBmt-, B is a residue as defined under 1b above, e.g. of formula III" as defined above, X is -Sar- and Y is -Val-.

Examples of such cyclosporins suitable for use in accordance with the present invention are:

1.35 [O-Acetyl-Thr]$^2$-Ciclosporin; and
1.36 1,2-Ethanedicarboxylic acid [O-threonyl]$^2$-Ciclosporin di-ester.

Cyclosporin 1.36 has the formula VI

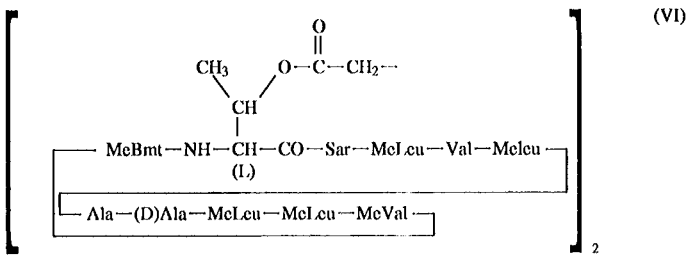

A further preferred group of cyclosporins of CLASS 1 are those:

1c) Wherein the 3'-carbon atom of the residue at the 1-position is oxo substituted.

When the 3'-carbon atom of the residue at the 1-position is oxo substituted this is suitably -3'-desoxy-3'-oxo-McBmt- of formula VII

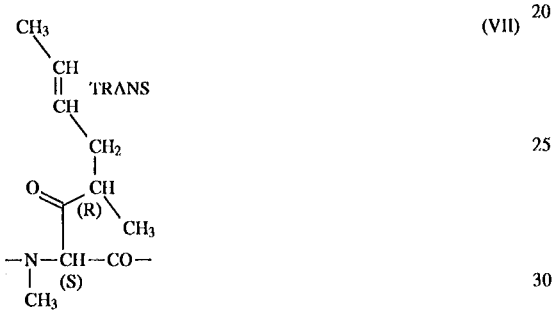

Especially preferred cyclosporins of this group are those of formula II as illustrated above, wherein A is a residue of formula VII above, B has the meanings given for formula II, X is -Sar- and Y is -Val-.

A yet further group of cyclosporins of CLASS I are those:

1d) Wherein the β-carbon atom of the residue at the 2-position is β-oxo substituted, i.e. wherein the residue at the 2-position is a β-oxo-α-amino acid residue.

When the residue at the 2-position is a β-oxo-α-amino acid residue, this residue will generally have the (L) configuration. Suitably it is -α-methylketo-Gly- of formula VIII

Examples of cyclosporins belonging to groups 1c and 1d, suitable for use in accordance with the present invention are:

1.37 [3'-Desoxy-3'-oxo-MeBmt]$^1$-Ciclosporin;
1.38 [3'-Desoxy-3'-oxo-MeBmt]$^1$-[Val]$^2$-Ciclosporin;
1.39 [3'-Desoxy-3'-oxo-MeBmt]$^1$-[Nva]$^2$-Ciclosporin;
1.40 [α-Methylketo-Gly]$^2$-Ciclosporin; and
1.41 [Dihydro-McBmt]$^1$-[α-methylketo-Gly]$^2$-Ciclosporin.

Cyclosporins 1.37 to 1.39 are especially preferred.

Class 2

A cyclosporin wherein:

i) The 3'-carbon atom of the residue at the 1-position is $C_{1-4}$alkoxyimino substituted, e.g. a cyclosporin wherein the residue at the 1-position is a -3'-desoxy-3'-($C_{1-4}$alkoxyimino)-McBmt- residue; or ii) The residue at the 2-position is an (L)-isoleucyl residue; or iii) The residue at the 11-position is an N-methyl-(L)-alanyl, N-methyl-(L)-isoleucyl or N-methyl-(L)-alloisoleucyl or N-methyl-(L)-leucyl residue.

-3'-Desoxy-3'-($C_{1-4}$alkoxyimino)-McBmt- residues as defined under (i) above have the formula IX

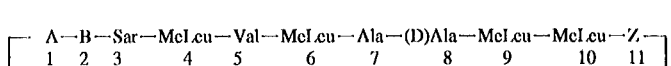

Wherein $R_9$ is $C_{1-4}$alkyl.

Alkyl groups as $R_9$ may be branched or straight chain. Preferably they are straight chain.

By N-methyl-(L)-alloisoleucyl (-MealloIle-) as used under (iii) above is meant the residue of formula X

[formula X image]

Preferred cyclosporins of this class are those of formula XI

[formula XI image]

wherein

A is -McBmt-, -dihydro-McBmt- or a residue as defined under (i) above,

B is -αAbu-, -Thr-, -Val- or -Nva- or additionally, when
A is -McBmt- or -dihydro-McBmt-, -Ile-, and
when
A is -McBmt- or -dihydro-McBmt- and
B is -αAbu-, -Thr-, -Val- or -Nva-,
Z is -McAla-, -MeIle-, -MealloIle- or -MeLeu-, or
when
A is a residue as defined under (i) above or
when
B is -Ile-, Z is -MeVal-.

Examples of such cyclosporins suitable for use in accordance with the present invention are:

2.1 [3'-Desoxy-3'-methoxyimino-MeBmt]$^1$-Ciclosporin;
2.2 [Ile]$^2$-Ciclosporin;
2.3 [MeAla]$^{11}$-Ciclosporin;
2.4 [MeIle]$^{11}$-Ciclosporin; and
2.5 [MealloIle]$^{11}$-Ciclosporin; and
2.6 [MeLeu]$^{11}$-Ciclosporin.

Of this class, cyclosporins wherein the residue at the 2-position has the meaning given under (ii) above, especially cyclosporin 2.2, are preferred.

Cyclosporins wherein the residue at the 11-position has the meaning given under (iii) above, e.g. cyclosporins 2.4 and 2.5, are also of particular interest.

Class 3

Cyclosporins of formula XI as illustrated above wherein:

Z is -Val- or -MeVal-:
when
Z is -Val-,
A is -MeBmt- or -dihydro-MeBmt-; or
when
Z is -MeVal-
A is -3'-desoxy-MeBmt-, 3'-desoxy-dihydro-MeBmt-, -N-desmethyl-MeBmt-, -N-desmethyl-dihydro-MeBmt-, -3'-desoxy-4'-desmethyl-dihydro-MeBmt- or -MeLeu-:
and
when
Z is -Val-,
B is -αAbu- or -Thr-;
when
Z is -MeVal- and
A is -3'-desoxy-MeBmt-, -3'-desoxy-dihydro-MeBmt-, -3'-desoxy- 4'-desmethyl-dihydro-MeBmt- or -MeLeu-,
B is -αAbu-; or
when
Z is -MeVal- and
A is -N-desmethyl-MeBmt- or -N-desmethyl-dihydro-MeBmt-,
B is -Thr-.

Cyclosporins of this class are:

3.1. [Val]$^{11}$-Ciclosporin (also known as cyclosporin E);
3.2. [Dihydro-MeBmt]$^1$-[Val]$^{11}$-Ciclosporin (or dihydrocyclosporin E);
3.3. [3'-Desoxy-MeBmt]$^1$-Ciclosporin (or cyclosporin F);
3.4. [3'-Desoxy-dihydro-MeBmt]$^1$-Ciclosporin (or dihydrocyclosporin F);
3.5. [N-Desmethyl-MeBmt]$^1$-[Thr]$^2$-Ciclosporin (or cyclosporin P);
3.6. [N-Desmethyl-dihydro-MeBmt]$^1$-[Thr]$^2$-Ciclosporin (or dihydrocyclosporin P);
3.7. [Thr]$^2$-[Val]$^{11}$-Ciclosporin (or cyclosporin W);
3.8. [Dihydro-MeBmt]$^1$-[Thr]$^2$-[Val]$^{11}$-Ciclosporin (or dihydrocyclosporin W);
3.9. [3'-Desoxy-4'-desmethyl-dihydro-MeBmt]$^1$-Ciclosporin (or cyclosporin Z);
3.10. [MeLeu]$^1$-Ciclosporin (or cyclosporin 28).

Various acylated cyclosporins of group 1a), in particular group 1a$^1$), and group 1b) are known. Thus cyclosporins 1.1, 1.4, 1.8, 1.9, 1.13, 1.14 and 1.34 are known from and are described, together with processes for their production, e.g. from Traber et al., Helv. Chim. Acta, 60, 1247 et seq. (1977), 65, 1655 et seq. (1982), 70, 13 et seq. (1987); Kobel et al., Europ. J. Applied Microbiology, Biotechnology 14, 273 et seq. (1982); and von Wartburg et al., Progress in Allergy, 38, 28 et seq. (1986).

Cyclosporins 1.2, 1.3, 1.5, 1.6, 1.7 and 1.10 are new and form part of the present invention as novel compounds per se. Cyclosporins 1.2, 1.5 to 1.7 and 1.10 may be prepared analogously to the methods described in the art, e.g. for the preparation of cyclosporin 1.1., by acetylation of the corresponding cyclosporins wherein the residue at the 1-position is -MeBmt- or -dihydro-MeBmt-. The cyclosporin starting materials are known, in the case of cyclosporins 1.6 and 1.7 from e.g. European patent publication no. 0 194 972. The product cyclosporins have the following physical characteristics:

| | Physical data: |
|---|---|
| 1.2 | $[\alpha]_D^{20} = -328°$ (c = 0.97 in CHCl$_3$) |
| 1.5 | $[\alpha]_D^{20} = -250°$ (c = 1.0 in CHCl$_3$) |
| 1.6 | $[\alpha]_D^{20} = -302.6°$ (c = 0.5 in CHCl$_3$) |
| 1.7 | $[\alpha]_D^{20} = -296.2°$ (c = 0.5 in CHCl$_3$) |
| 1.10 | $[\alpha]_D^{20} = -293°$ (c = 0.55 in CHCl$_3$) |

In general, when the residue at the 2-position in the cyclosporin starting material is a β-hydroxy-αamino acid residue, for example -Thr-, the β-OH group at this position will be more readily susceptible to reaction than the 3'-hydroxy, e.g. of -MeBmt- or -dihydro-MeBmt-, at the 1-position. Cyclosporins wherein the residue at the 2-position, but not the residue at the 1-position, is acylated [as in the case of group 1b) cyclosporins, for example cyclosporin 1.35] or wherein both the residue at the 1- and 2-position is acylated [as in the case of cyclosporins 1.13 and 1.14 of group 1a$^1$] may thus be readily obtained, according to, or analogously to, the methods described in the art, taking advantage of this relative difference in reactivity. To produce cyclosporins wherein the 1-position is 3'-O-acylated but having a free β-OH group at 2-position [as in the case of cyclosporin 1.3] it is first necessary to protect the hydroxy group at the 2-position and then remove the protecting group subsequent to acylation of the residue at the 1-position. The following example is illustrative of the general procedure:

EXAMPLE A

Preparation of [3'-O-acetyl-MeBmt]$^1$-[Thr]$^2$-Ciclosporin (Cyclosporin 1.3):

Step 1: introduction of an O-protecting group at -Thr-$^2$ of [Thr]$^2$-Ciclosporin 6.09 g of [Thr]$^2$-Ciclosporin are dissolved in 25 ml abs. CH$_2$Cl$_2$ and 5 ml ethinyl-ether and 0.2 ml trifluoroacetic acid are added. The reaction mixture is stirred for 20 hrs. at room temperature under an atmosphere of nitrogen. The reaction mixture is shaken with cold, 20% KHCO$_3$, washed with water, extracted with CH$_2$Cl$_2$, dried over MgSO$_4$, filtered and evaporated. The obtained foam is purified chromatographically using 440 g silica gel (0.04–0.06) using toluene/acetone (2:1) as eluant and collecting in 500 ml fractions. The product, [Thr-1-methyl-ethoxymethyl ether]$^2$-Ciclosporin is recovered from fractions 26 to 29: m.p. =76.6° C.

Step 2: acylation of [Thr]$^2$-Ciclosporin in -Thr-$^2$O-protected form 10.66 g of the product of step 1, 106 ml acetic acid anhydride and 1.22 g of 4-dimethylaminopyridine are combined and stirred for 20 hrs. at room temperature and taken up with toluene at 40° C. The residue is dissolved in 400 ml toluene and extracted 1× with 250 ml cold acetic acid, 1× with 250 ml H₂O, 1× with 200 ml cold 20% KHCO₃ and 1× with 250 ml H₂O. The toluene extracts are dried over MgSO₄, filtered evaporated and dried under vacuum to yield [3'-O-acetyl-McBmt]¹-[Thr-1-methyl-ethoxymethyl ether]²-Ciclosporin.

Step 3: deprotection of [3'-O-acetyl -McBmt]¹-[Thr]²-Ciclosporin in -Thr-² O-protected form 11.38 g of the product of step 2, 80 ml tetrahydrofuran and 160 ml 67% acetic acid are stirred for 48 hrs. at room temperature under N₂. The reaction mixture is taken up in toluene, the residue dissolved in toluene, shaken with 20% KHCO₃, washed with H₂O and the toluene extracts dried over MgSO₄ and filtered. The filtrate is evaporated and purified chromatographically using 440 g silica gel (0.04–0.06) using toluene/acetone (3:1) as eluant and collecting in 500 ml fractions. The end-product, [3'-O-acetyl-MeBmt]¹-[Thr]²-Ciclosporin is recovered from fractions 5–9: m.p.=75.6° C., $[\alpha]_D^{20}$=−275.5° (c=0.65 in CHCl₃).

Cyclosporins of formula II' are new and form part of the present invention as novel compounds per se. Accordingly in a further aspect the present invention provides, as a novel group of cyclosporins, those:

1a⁴) Of the formula II' as hereinbefore defined.

Cyclosporins of group 1a⁴) may be prepared entirely analogously to the procedures for the production of known cyclosporins 1.1, 1.4 etc., hereinbefore referred to or anlogously to the production of cyclosporin 1.3, starting from the corresponding cyclosporins wherein the residue at the 1-position is -McBmt- or -dihydro-McBmt. Required starting materials are known and described, together with the methods for their production, e.g. in UK patent application no. 2 155 936, U.S. Pat. No. 4,639,434 and European patent publication no. 0 056 782. As indicated above, cyclosporins of formula II', wherein W is the residue of a β-hydroxy-(rather than β-O-acyl-) -α-amino acid residue are prepared analogously e.g. to example A, by first protecting at the 8-position, acylating at the 1-position and then de-protecting at the 8-position.

Cyclosporin 1.15 of group 1a⁴) has the following characterising data: $[\alpha]_D^{20}$=−272° (c=1.0 in CHCl₃).

Cyclosporins wherein the 3'-carbon atom of the residue at the 1-position is azidoalkylcarbonyloxy or alkoxycarbonyloxy substituted are also new and form part of the present invention as novel compounds per se.

A group of cyclosporins of this type comprises those:

1a⁵) Wherein the residue at the 1-position is a -3'-O-(C₁₋₄-azidoalkyl)-carbonyl- or -3'-O-(C₁₋₄alkoxy)-carbonyl--McBmt- or -dihydro-McBmt- residue, i.e. of formula I as illustrated above, wherein ACYL¹ is a group of formula R₁'—CO— or R₂—O—CO— wherein R₁' is C₁₋₄azidoalkyl and R₂ is C₁₋₄alkyl.

Preferred cyclosporins of this group are those of formula II as illustrated above, wherein A is a residue as defined under 1a⁵ above, B has the meanings given for formula II, X is -Sar- and Y is -Val-.

The present invention also provides a process for the production of cyclosporins of group 1a⁵) which process comprises:

a) reacting the corresponding cyclosporin wherein the residue at the 1-position is -McBmt- or -dihydro-McBmt- with a compound of formula XII or XIII.

R₁'—CO—Q    (XII)

R₂—O—CO—Q    (XIII)

Wherein R₁' and R₂ have the meanings given above and Q is a leaving group.

Q is suitably halogen or —OH. When Q is halogen, reaction is suitably carried out e.g. in the presence of a catalyst such as n-butyllithium. When Q is —OH reaction is suitably carried out in the presence of an activating agent. Reaction is suitably performed at temperatures of from ca −100° to −50° C., e.g. as described in the following examples B:

EXAMPLES B

1. Preparation of [3'-O-methoxycarbonyl-McBmt]¹-Ciclosporin (cyclosporin 1.11)

3.76 ml of a 1.48M solution of n-butyllithium in 3.76 ml hexane are added to 0.87 ml diisopropylamine in tetrahydrofuran at −78° and the whole stirred for 30 min. at −78° C. 1.0 g Ciclosporin in 15 ml dry tetrahydrofuran are added at the same temperature and stirring continued for a further 30 min. 0.326 ml methyl chloroformate are added and stirring continued for a further 1 hour at −78° C. The temperature is then allowed to rise to room temperature. 10 ml of water are added and most of the tetrahydrofuran removed by evaporation. The residue is taken up in 100 ml ethyl ether and 50 ml water, the aqueous layer separated and extracted 2× with ethyl ether. The combined organic extracts are dried over MgSO₄ and evaporated to dryness. The residue is purified chromatographically on silica gel, eluting with ethyl acetate, to yield the title compound: $[\alpha]_D^{20}$=−234° (c=1.0 in CHCl₃).

2. Preparation of [3'-O-(4-azidobutanoyl)-McBmt]¹-Ciclosporin (cyclosporin 1.12)

7.74 g γ-azidobutyric acid, 8.6 g 4-dimethylaminopyridine and 5.11 g Mullayama-reagent (2-chloro-1-methylpyridinium iodide) are added to 12.02 g Ciclosporin in 200 ml abs. CH₂Cl₂, and the reaction mixture is stirred for 90 hrs. at room temperature. The obtained product is diluted with CH₂Cl₂ shaken with 100 ml ice-cold, 10% NaOH, 200 ml H₂O and 200 ml 10% acetic acid washed with water, and the organic phases are dried over Na₂SO₄. The filtrate is evaporated and dried again. The product is purified chromatographically using 1.2 kg silica gel (0.04–0.06 mm) using hexane/acetone (3:1) as eluant collecting in fractions of 250 ml up to fraction 20 and then hexane/acetone (7:3), collecting in fractions of 300 ml thereafter. The title compound is recovered from fractions 23–27: $[\alpha]_D^{20}$=−289.8° (c=0.5 in CHCl₃).

Cyclosporins of group 1a² as hereinbefore set forth are also new and form part of the present invention as novel compounds per se.

The present invention also provides a process for the production of cyclosporins of group 1a²) which process comprises:

b) acylating the corresponding cyclosporin wherein the residue at the 1-position is an -8'-C₁₋₈-alkoxy-cis-McBmt- or -8'-C₁₋₈-alkoxy-dihydro-McBmt- residue of formula XIV

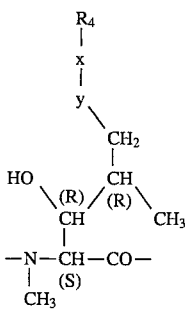

(XIV)

wherein —x—y— and $R_4$ have the meanings given above for formula IV, for example acylating a cyclosporin of formula II as illustrated above wherein A is a residue of formula XIV as defined above, B has the meanings given for formula II, X is -Sar- and Y is -Val-, e.g. by reaction with a compound of formula XV $$R_5\text{—CO—Q} \qquad \text{(XV)}$$

wherein $R_5$ is $C_{1-4}$alkyl and Q is a leaving group, for example a halogen atom; or c) for the preparation of a cyclosporin of group $1a^2$ wherein the residue at the 1-position is a -3'-O-acyl-8'-$C_{1-8}$-alkoxy-cis-MeBmt- residue of formula IV as illustrated above, wherein —x—y— is cis —CH=CH—, $R_4$ has the meaning given for formula IV and $ACYL^1$ is an acyl O-protecting group, for example acetyl, reacting a cyclosporin wherein the residue at the 1-position is a -3'-O-acyl-5'-des-(1-propenyl)-5'-formyl-MeBmt- residue of formula XVI

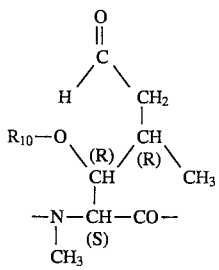

(XVI)

wherein $R_{10}$ is an acyl O-protecting group, e.g. acetyl, for example a cyclosporin of formula II as illustrated above wherein A is a residue of formula XVI as defined above, B has the meanings given for formula II, X is -Sar- and Y is -Val-, with a compound of formula XVII

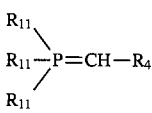

(XVII)

wherein each $R_{11}$ is phenyl or $C_{1-4}$alkyl and $R_4$ has the meaning given for formula IV.

Reaction in accordance with process step (c) above may be carried out in accordance with standard methods employed for effecting a Wittig reaction, e.g. under anhydrous conditions, for example in an inert solvent or diluent such as absolute benzene, tetrahydrofuran, ethyl-ether or toluene, at a temperature of from about −80° C. to 20° C., optionally in the presence of a salt, e.g. an alkali-metal halogenide. The reaction is suitably carried out under an inert atmosphere.

The cyclosporin starting materials required for process step (c) may be obtained from the corresponding cyclosporins wherein the residue at the 1-position is -3'-O-acyl-protected-MeBmt-, for example -3'-O-acetyl-MeBmt- by:

d) ozonolysation and treatment of the immediately obtained ozonolysis product with a mild reducing agent.

Ozonolysis in accordance with reaction step (d) may be carried out in accordance with standard techniques, e.g. in an ozonisor in the presence of, e.g. ethyl acetate or dichloromethane, at a temperature of from about −90° to about −40° C. A suitable mild reducing agent is dimethyl sulfide. Suitably, ozonolysis and treatment with the mild reducing agent is carried out in a single reaction vessel, e.g. as described in the following examples C.

The starting materials for process step (d) are cyclosporins of group $1a^1$ and are known or may be obtained as hereinbefore described.

Process step (b) may be carried out analogously to processes for the production of cyclosporins of groups $1a^1$) and 1b) as hereinbefore described, e.g. with reference to the literature. Similarly cyclosporins of group $1a^2$) having a free β-hydroxy-α-amino acid residue, e.g. -Thr-, at the 2-position may be produced by intermediate protection and subsequent deprotection of the β-OH group, e.g. proceeding analogously to the methods described in relation to example A above. The starting materials for process step (b) above may be obtained by:

e) deprotection of the corresponding cyclosporin wherein the residue at the 1-position is an -8'-$C_{1-8}$alkoxy-cis-MeBmt- or -8'-$C_{1-8}$alkoxy-dihydro-MeBmt- residue in 3'-O-protected form; or f) reduction of the corresponding cyclosporin wherein the residue at the 1-position is an -8'-$C_{1-8}$alkoxy-cis-MeBmt- residue in free or 3'-O-protected form and, when required, carrying out process step (e).

Suitable 3'-O-protecting groups in the starting materials for process step (e) include any of those known and commonly employed in the art of peptide chemistry including acyl and ether protecting groups. The starting materials for process step (e) thus include the products of process step (c) hereinbefore described. Corresponding starting materials wherein the 3'-O-protecting group is other than acyl may be obtained analogously to process steps (d) and (c) starting from the appropriate 3'-O-protected cyclosporins.

Process step (e) itself can be carried out in accordance with procedures commonly employed in the art of peptide chemistry, e.g. by hydrolysis in the presence of a base such as an alkali metal alkoxide or carbonate to remove acetyl protecting groups or hydrolytic ether cleavage, e.g. in the presence of trifluoro-acetic acid or HCl to remove protecting ether groups. Process step (e) is suitably conducted at temperatures of from about −20° to about 20° C., e.g. as hereinafter described in examples D.

Process step (f) may also be carried out analogously to known methods, e.g. for reducing naturally occuring cyclosporins to the corresponding dihydrocyclosporins, for example by catalytic hydrogenation, e.g. in accordance with the general methods disclosed in U.K. Patent Specification No. 1 567 201. Hydrogenation is suitably effected under neutral pH conditions at temperatures of from about 20° to about 30° C. and at atmospheric or slightly elevated pressure, in the presence of a catalyst such as platinum or, preferably, paladium (e.g. paladium on charcoal) in the presence of an inert solvent or diluent such as ethyl acetate or lower aliphatic alkanols such as methanol and isopropanol.

The cyclosporin starting materials for process step (b) are also new and form part of the present invention as novel compounds per se. In a further aspect the present invention accordingly also provides:

Class 4

A cyclosporin wherein the residue at the 1-position is an -8'-alkoxy-cis-McBmt- or -8'-$C_{1-8}$-alkoxy-dihydro-McBmt- residue of formula XIV as defined above.

Preferred cyclosporins of this class are those of formula II as defined for process step (b).

In addition to their utility as intermediates, cyclosporins of class 4 also possess, e.g. immunosuppressive, anti-inflammatory and anti-parasitic activity as hereinafter described. The said cyclosporins thus have utility in their own right.

Cyclosporins of class 4 also exhibit activity in increasing sensitivity to, or increasing the efficacy of, chemotherapeutic drug therapy and, in particular in reversing chemotherapeutic drug resistance, e.g. resistance to anti-neoplastic or cytostatic chemotherapy, as herein disclosed for cyclosporins of classes 1 to 3. Having regard e.g. to their inherent immunosuppressive properties however, cyclosporins of class 4 are generally less suitable for use in such indications.

The cyclosporin starting materials for process step (c) are also new and form part of the present invention as novel compounds per se. These starting materials may, of course, be subjected to intervening de-protection and/or re-protection, e.g. for the purposes of handling, transport or storage, in accordance with methods known or practiced in the art. In a yet further aspect the present invention accordingly also provides:

Class 5

A cyclosporin wherein the residue at the 1-position is -5'-des-(1-propenyl)-5'-formyl-McBmt- in free or in 3'-O-protected form, i.e. a residue of formula XVIII

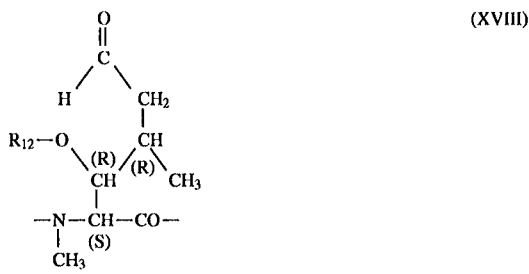

(XVIII)

wherein $R_{12}$ is hydrogen or an O-protecting group.

Preferred protecting groups as $R_{12}$ are acyl O-protecting groups, e.g. acetyl. Preferred cyclosporins of this class are those of the formula II as illustrated above, wherein A is a residue of formula XVIII as defined above, B has the meanings given for formula II, X is -Sar- and Y is -Val-.

When $R_{12}$ is hydrogen, the residue of formula XVIII also exists in the cyclic tautomeric form of formula XVIII':

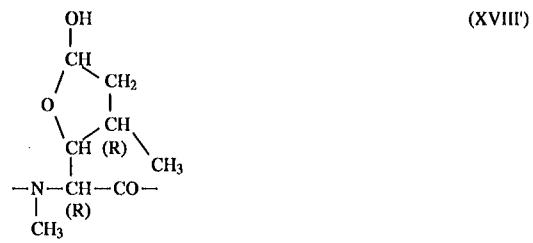

(XVIII')

Such tautomers are to be understood as being within the purview of the present invention, e.g. embraced by the definition for class 5 cyclosporins above.

The following examples are illustrative of the above processes for the preparation of cyclosporins of group 1a² and of classes 4 and 5.

EXAMPLES C

Preparation of cyclosporins of group 1a².
Preparation of [3'-O-acetyl-$_8$'-methoxy-cis-McBmt]¹-Ciclosporin (cyclosporin 1.16):

16 g Methoxymethyltriphenylphosphoniumbromide are suspended in 270 ml absolute tetrahydrofuran (THF) in argon and cooled to −75° C. A solution of 5 g potassium t.butylate in 200 ml absolute THF is added dropwise over 30 minutes and the mixture is stirred again. After 2 hours a solution of 10 g of [3'-O-acetyl-5'-des-(1-propenyl)-5'-formyl-McBmt]¹-Ciclosporin in 25 ml THF is added dropwise over 20 minutes. The mixture is stirred for 4 hours at room temperature, then treated with 400 ml ethyl acetate. The extracts are washed with 2N HCl solution, saturated NaHCO₃ and saturated brine. The concentrated filtrate is chromatographed on 1.2 kg and 0.44 kg silica gel (0.04 to 0.063 mm) with CHCl₃ (10–40%) acetone/ethyl acetate to give the title compound: $[\alpha]_D^{20} = -267°$ (c=0.53 in CHCl₃).

Cyclosporins 1.17 to 1.21 may be prepared analogously. These have the following physical characteristics:

|      | Physical data: |
|------|----------------|
| 1.17 | $[\alpha]_D^{20} = -283°$ (c = 0.544 in CHCl₃) |
| 1.18 | $[\alpha]_D^{20} = -209.1°$ (c = 0.605 in CHCl₃) |
| 1.19 | $[\alpha]_D^{20} = -282.96°$ (c = 0.405 in CHCl₃) |
| 1.20 | $[\alpha]_D^{20} = -268°$ (c = 0.615 in CHCl₃) |
| 1.21 | $[\alpha]_D^{20} = -248.7°$ (c = 0.65 in CHCl₃) |

The starting material for the above process, which is a cyclosporin of class 5, is produced as follows:
Production of [3'-O-acetyl-5'-des-(1-propenyl)-5'-formyl-McBmt]¹-Ciclosporin (cyclosporin 5.1):

48.5 g of [3'-O-acetyl-McBmt]¹-Ciclosporin in 70 ml ethyl acetate are ozonised for 45 mins. at −70° C., using a Fischer ozone generator at 0.4 atm. with a current flow of 110 l/h. The obtained solution is gassed with N₂ and 9.8 ml dimethylsulfide are added. The solution is stirred for 2 hrs. at room temperature, concentrated by evaporation, washed 2x with benzene and dried under high vacuum to yield the desired product. This is used directly for further reaction without further purification: $[\alpha]_D^{20} = -302°$ (c=1.15 in CHCl₃).

The following cyclosporins are obtained analogously
5.2 [3'-O-acetyl-5'-des-(1-propenyl)-5'-formyl-McBmt]¹-[O-acetyl-Thr]²-Ciclosporin: $[\alpha]_D^{20} = -272.6°$ (c=0.504 in CHCl₃), m.p.=156°–160°
5.3 [3'-O-acetyl-5'-des-(1-propenyl)-5'-formyl-McBmt]¹-[Val]²-Ciclosporin: $[\alpha]_D^{20} = -306°$ (c=1.03 in CHCl₃), m.p.=168°–170°
5.4 [3'-O-acetyl-5'-des-(1-propenyl)-5'-formyl-McBmt]¹-[Nva]²-Ciclosporin: $[\alpha]_D^{20} = -291.76°$ (c=0.51 in CHCl₃).

EXAMPLES D

Preparation of cyclosporins of class 4.
Preparation of [8'-methoxy-cis-McBmt]¹-Ciclosporin (cyclosporin 4.1): 4 g of cyclosporin 1.16 (from examples C) in 41 ml methanol/water (5:1) are heated with 3.5 g potassium carbonate and stirred at room temperature. After 21 hours the cooled solution is made acid with 10% tartaric acid solution and extracted three times with CHCl₃. The extracts are washed with saturated NaHCO₃ and water and dried over $Na_2SO_4$ and concentrated. Chromatogrphy on 220 g silica gel with ethyl acetate and ethyl acetate/hexane (100 to 20%) gives the title compound: $[\alpha]_D^{20}=-239°$ (c=0.53 in $CHCl_3$).

The following cyclosporins are obtained analogously:

4.2 [8'-t.Butoxy-cis-MeBmt]$^1$-Ciclosporin: $[\alpha]_D^{20}=-228°$ (c=0.5 in $CHCl_3$);

4.3 [8'-Methoxy-cis-MeBmt]$^1$-[Thr]$^2$-Ciclosporin: $[\alpha]_D^{20}=-220°$ (c=0.37 in $CHCl_3$);

4.4 [8'-t.Butoxy-cis-MeBmt]$^1$-[Thr]$^2$-Ciclosporin: $[\alpha]_D^{20}=-221°$ (c=0.43 in $CHCl_3$);

4.5 [8'-Methoxy-cis-MeBmt]$^1$-[Val]$^2$-Ciclosporin: $[\alpha]_D^{20}=-241°$ (c=0.54 in $CHCl_3$);

4.6 [8'-Methoxy-cis-MeBmt]$^1$-[Nva]$^2$-Ciclosporin: $[\alpha]_D^{20}=-236°$ (c=0.634 in $CHCl_3$);

Production of [8'-methoxy-dihydro-MeBmt]$^1$-Ciclosporin (cyclosporin 4.7).

302 mg of cyclosporin 4.1 are dissolved in 10 ml abs. ethanol and hydrogenated at room temperature and atmosperic pressure over 5% Pd on charcoal. After the uptake of the theoretical amount of hydrogen (50 min.), the catalyst is separated by filtration over hyflo, and the solvent evaporated at reduced pressure. The residue is chromatographed on 70 g silica gel (O=0.015 mm) with hexane-acetone (1:1) yielding the title compound: $[\alpha]_D^{20}=-229°$ (c=0.52 in $CHCl_3$).

The following cyclosporins are obtained analogously:

4.8 [8'-Methoxy-dihydro-MeBmt]$^1$-[Thr]$^2$-Ciclosporin: $[\alpha]_D^{20}=-217.5°$ (c=0.32 in $CHCl_3$);

4.9 [8'-Methoxy-dihydro-MeBmt]$^1$-[Val]$^2$-Ciclosporin: $[\alpha]_D^{20}=-223.6°$ (c=0.58 in $CHCl_3$);

4.10 [8'-Methoxy-dihydro-MeBmt]$^1$-[Nva]$^2$-Ciclosporin: $[\alpha]_D^{20}=-221.5°$ (c=0.594 in $CHCl_3$)

Cyclosporins of group $1a^3$ as hereinbefore set forth are also new and form part of the present invention as novel compounds per se.

The present invention also provides a process for the production of cyclosporins of group $1a^3$, which process comprises:

g) acylating the corresponding cyclosporin wherein the residue at the 1-position is -cis-MeBmt-; a -7'-desmethyl-7'-hydrocarbyl- -MeBmt- or -cis-MeBmt- residue wherein the hydrocarbyl moiety comprises at least two carbon atoms; or a -7'-desmethyl-7'-hydrocarbyl-dihydro-MeBmt- residue wherein the hydrocarbyl moiety comprises at least two carbon atoms and wherein any aliphatic group or moiety present as or in said hydrocarbyl moiety is saturated, which residue may be represented by the formula XIX

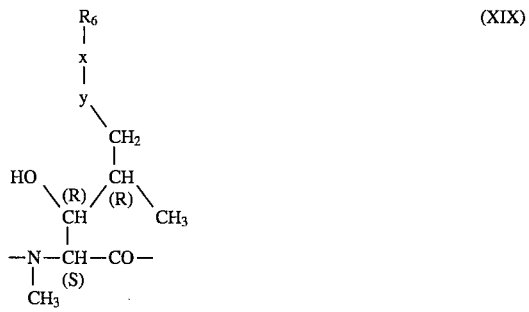

wherein —x—y— and $R_6$ have the meanings given above for formula V, for example, acylating a cyclosporin of formula II as illustrated above wherein A is a residue of formula XIX as defined above, B has the meanings given for formula II, X is -Sar- and Y is -Val-, e.g. by reaction with a compound of formula XV as defined above; or h) for the preparation of a cyclosporin of group $1a^3$ wherein the residue at the 1-position is -3'-O-acyl-cis-MeBmt- wherein the acyl moiety is an acyl O-protecting group, or a -7'-desmethyl-7'-hydrocarbyl- -MeBmt- or -cis-MeBmt- residue wherein the hydrocarbyl moiety comprises at least two carbon atoms and wherein the O-acyl moiety is an acyl O-protecting group, which residue may be represented by the formula V as illustrated above wherein —x—y— is cis or trans —CH=CH—, $R_6$ has the meaning given for formula V and $ACYL^1$ is an acyl O-protecting group, for example acetyl, reacting a cyclosporin wherein the residue at the 1-position is a -3'-O-acyl-5'-des-(1-propenyl)-5'-formyl-MeBmt- residue of formula XVI as defined above, for example a cyclosporin of formula II as illustrated above, wherein A is a residue of formula XVI as defined above, B has the meanings given for formula II, X is -Sar- and Y is -Val-, with a compound of formula XX

Wherein each $R_{11}$ is phenyl or $C_{1-4}$alkyl and $R_6'$ is hydrocarbyl of at least 2 carbon atoms and, when required, isolating the desired reaction product.

Process steps (g) and (h) may be carried out in exactly analogous fashion to process steps (b) and (c) above, for example as hereinafter described in examples E below. The starting materials for process step (g) may be obtained entirely analogously to process step (e) or (f) above by:

i) deprotection of the corresponding cyclosporin wherein the residue at the 1-position is -3'-O-acyl-cis-MeBmt- or, a -7'-desmethyl-7'-hydrocarbyl- -MeBmt- or -cis-MeBmt- residue wherein the hydrocarbyl moiety comprises at least two carbon atoms, said residue being in 3'-O-protected form; or j) reduction of the corresponding cyclosporin wherein the residue at the 1-position is a -7'-desmethyl-7'-hydrocarbyl- -MeBmt- or -cis-MeBmt- residue, said residue being in free or 3'-O-protected form and, when required, carrying out process step (i).

Suitable 3'-O-protecting groups are as hereinbefore described in relation to process steps (e) and (f). In carrying out process step (j) unsaturated linkages in the hydrocarbyl moiety will undergo reduction, together with the group —x—y—. Alternatively, cyclosporin starting materials wherein the residue at the 1-position is -cis-MeBmt- may be obtained in accordance with the total synthetic method for the production of cyclosporins, e.g. as described in European patent publication no. 0 034 567 or U.S. Pat. No. 4,369,542.

The cyclosporin starting materials for process step (g) wherein the residue at the 1-position is other than -cis-MeBmt- are also new and form part of the present invention as novel compounds per se. In a further aspect the present invention accordingly also provides:

Class 6

A cyclosporin wherein the residue at the 1-position is a -7'-desmethyl-7'-hydrocarbyl- -MeBmt- or -cis-MeBmt- residue wherein the hydrocarbyl moiety comprises at least two carbon atoms, or a -7'-desmethyl-7'-hydrocarbyl-dihydro-MeBmt- residue wherein the hydrocarbyl moiety comprises at least two carbon atoms and wherein any aliphatic group or moiety as or in said hydrocarbyl moiety is saturated, which residue may be represented by formula XIX'

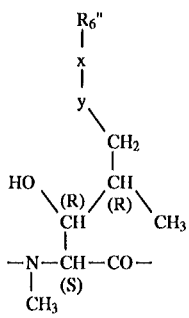

(XIX')

wherein

—x—y— is cis or trans —CH=CH— or —CH$_2$—CH$_2$— and R$_6$" is hydrocarbyl having at least two carbon atoms with the proviso that when —x—y— is —CH$_2$—CH$_2$— any aliphatic group or moiety present as or in R$_6$" is saturated.

Preferred cyclosporins of this class are those of formula II as illustrated above wherein A is a residue of formula XIX' as defined above, B has the meanings given for formula II, X is -Sar- and Y is -Val-.

In addition to their utility as intermediates, cyclosporins of class 6 also possess, e.g. immunosuppressive, anti-inflammatory and anti-parasitic activity as hereinafter described. The said cyclosporins thus have utility in their own right.

Cyclosporins of class 6 also exhibit activity in increasing sensitivity to, or increasing the efficacy of, chemotherapeutic drug therapy and, in particular in reversing chemotherapeutic drug resistance, e.g. anti-neoplastic or cytostatic chemotherapy, as hereinbefore discussed for cyclosporins of classes 1 to 3. Having regard, e.g. to their inherent immunosuppressive properties, however cyclosporins of class 6 are generally less suitable for use in such indications.

Cyclosporins as herein described and exemplified, wherein the residue at the 1-position is -cis-McBmt-, while within the purview of the aforementioned European patent publication no. 0 034 567 and U.S. Pat. No. 4,369,542, are formally novel.

The following examples are illustrative of the above processes for the preparation of cyclosporins of group 1a$^3$ and of class 6.

EXAMPLES E

Preparation of [3'-O-acetyl-7'-desmethyl-7'-phenyl-McBmt]$^1$-Ciclosporin (cyclosporin 1.22) and of [3'-O-acetyl-7'-desmethyl-7'-phenyl-cis-McBmt]$^1$ -Ciclosporin (cyclosporin 1.27):

9.5 g Benzyltriphenylphosphoniumchloride are dissolved in 150 ml dry benzene and reacted with 2.7 g potassium-t.buylate for 24 hours under reflux on a water separator. After cooling, the suspension is filtered into a new flask under inert atmosphere. 5 g of cyclosporin 5.1 (c.f. examples C) in 50 ml benzene are added over a period of 5 minutes. After 21 hours at room temperature, the reaction mixture is poured on ice, the organic phase washed with 2N HCl, bicarbonate and water dried over sodium sulfate, and evaporated. The residue is chromatographed twice on 440 g silica gel (0.04–0.063 mm) with chloroform containing 8 to 30 p.p.vol. acetone. Fraction 2 contains cyclosporin 1.27 fractions 5–15 cyclosporin 1.22. Cyclosporins 1.23 to 1.26 and 1.28 to 1.34 may be prepared analogously. These cyclosporins have the following physical characteristics.

Physical data:

| | |
|---|---|
| 1.22 | $[\alpha]_D^{20} = -210.9°$ (c = 1.37 in CHCl$_3$) |
| 1.23 | $[\alpha]_D^{20} = -234.9°$ (c = 0.89 in CHCl$_3$) |
| 1.24 | $[\alpha]_D^{20} = -248.97°$ (c = 1.17 in CHCl$_3$) |
| 1.25 | $[\alpha]_D^{20} = -237.3°$ (c = 0.39 in CHCl$_3$) |
| 1.26 | NMR.IR { Ester 1740; Acetate 1230 } in CH$_2$Cl$_2$ |
| 1.27 | $[\alpha]_D^{20} = -235.8°$ (c = 1.0 in CHCl$_3$) |
| 1.28 | $[\alpha]_D^{20} = -220°$ (c = 1.75 in CHCl$_3$) |
| 1.29 | $[\alpha]_D^{20} = -239.07°$ (c = 0.97 in CHCl$_3$) |
| 1.30 | $[\alpha]_D^{20} = -207.8°$ (c = 1.25 in CHCl$_3$) |
| 1.31 | $[\alpha]_D^{20} = -239.6°$ (c = 0.91 in CHCl$_3$) |
| 1.32 | NMR.IR { Ester 1746; Acetate 1228; MH$^+$ 1271 } in CCl$_4$ |
| 1.33 | NMR.IR { Ester 1745; Acetate 1225; MH$^+$ 1271 } in CCl$_4$ |
| 1.34 | $[\alpha]_D^{20} = -226.23°$ (c = 1.447 in CHCl$_3$) |

EXAMPLES F

Preparation of cyclosporins of class 6.

Preparation of [7'-desmethyl-7'-phenyl-McBmt]$^1$-Ciclosporin (cyclosporin 6.1)

2.29 g of cyclosporin 1.22 obtained as above are dissolved in 20 ml methanol:water (4.5:1) containing 1.67 g potassium carbonate. After 20 hours at room temperature, the reaction mixture is poured on ice containing 10% of tartaric acid and extracted with chloroform. The crude extract is chromatographed on 120 g silica gel (0.04–0.063 mm) with dichloromethane, containing increasing amounts (20–30%) of acetone, to give the title compound: $[\alpha]_D^{20} = -209°$ (c=0.99 in CHCl$_3$).

The following cyclosporins are obtained analogously:
6.2 [7'-Desmethyl-7'-phenyl-cis-McBmt]$^1$-Ciclosporin: $[\alpha]_D^{20} = -236°$ (c=1 in CHCl$_3$);
6.3 [7'-Desmethyl-7'-vinyl-cis-McBmt]$^1$-Ciclosporin: $[\alpha]_D^{20} = -249°$ (c=1.17 in CHCl$_3$);
6.4 [7'-Desmethyl-7'-vinyl-cis-McBmt]$^1$-[Thr]$^2$-Ciclosporin: $[\alpha]_D^{20} = -248°$ (c=1.44 in CHCl$_3$);
6.5 [7'-Desmethyl-7'-(3-methyl-n.butyl)-cis-McBmt]$^1$-Ciclosporin: $[\alpha]_D^{20} = -240°$ (c=1.15 in CHCl$_3$);
6.6 [7'-Desmethyl-7'-n.propyl-cis-McBmt]$^1$-Ciclosporin: $[\alpha]_D^{20} = -220°$ (c=1.75 in CHCl$_3$);
6.7 [7'-Desmethyl-7'-(β-allyl)-cis-McBmt]$^1$-Ciclosporin: $[\alpha]_D^{20} = -239°$ (c=0.97 in CHCl$_3$);
6.8 [7'-Desmethyl-7'-phenyl-McBmt]$^1$[Val]$^2$-Ciclosporin: $[\alpha]_D^{20} = -208°$ (c=1.025 in CHCl$_3$);
6.9 [7'-Desmethyl-7'-phenyl-cis-McBmt]$^1$-[Val]$^2$-Ciclosporin: $[\alpha]_D^{20} = -240°$ (c=0.91 in CHCl$_3$);
6.10 [7'-Desmethyl-7'-vinyl-cis-McBmt]$^1$[Val]$^2$-Ciclosporin: $[\alpha]_D^{20} = -254.8°$ (c=0.48 in CHCl$_3$);
6.11 [7'-Desmethyl-7'-vinyl-cis-McBmt]$^1$[Nva]$^2$Ciclosporin: $[\alpha]_D^{20} = -246.1°$ (c=0.52 in CHCl$_3$);
6.12 [7'-Desmethyl-7'-(3-bromo-n.propyl)-cis-McBmt]$^1$-Ciclosporin: $[\alpha]_D^{20} = -226°$ (c=1.44 in CHCl$_3$);

De-protection of cyclosporin 1.23 leads to the production of [cis-McBmt]$^1$-Ciclosporin: $[\alpha]_D^{20} = -235°$ (c=0.9 in CHCl$_3$).

Preparation of [7'-Desmethyl-7'-phenyl-dihydro-McBmt]$^1$-Ciclosporin (cyclosporin 6.13)

796 mg of a mixture of cyclosporins 6.1 and 6.2 are hydrogenated in 50 ml ethanol over 100 mg 10% Pd on charcoal at room temperature during 6 hours. Filtration over Hyflo yields the pure title compound: $[\alpha]_D^{20}=-210°$ (c=0.7 in CHCl$_3$).

The following cyclosporins are obtained analogously:

6.14 [7'-Desmethyl-7'-n.propyl-dihydro-MeBmt]$^1$-Ciclosporin: $[\alpha]_D^{20}=-188°$ (c=6.16 in CHCl$_3$), obtained from cyclosporin 6.6 or 6.7;

6.15 [7'-Desmethyl-7'-ethyl-dihydro-MeBmt]$^1$-[Thr]$^2$-Ciclosporin: $[\alpha]_D^{20}=-224°$ (c=0.4 in CHCl$_3$), obtained from cyclosporin 6.4;

6.16 [7'-Desmethyl-7'-(3-methyl-n.butyl)-dihydro-MeBmt]$^1$-Ciclosporin: $[\alpha]_D^{20}=-222°$ (c=0.995 in CHCl$_3$), obtained from cyclosporin 6.5;

6.17 [7'-Desmethyl-7'-i.propyl-dihydro-MeBmt]$^1$-Ciclosporin: $[\alpha_D^{20}=-229°$ (c=1.32 in CHCl$_3$);

6.18 [7'-Desmethyl-7'-ethyl-dihydro-MeBmt]$^1$-[Val]$^2$-Ciclosporin: $[\alpha]_D^{20}=-232.9°$ (c=0.48 in CHCl$_3$), obtained from cyclosporin 6.10;

6.19 [7'-Desmethyl-7'-ethyl-dihydro-MeBmt]$^1$-[Nva]$^2$-Ciclosporin: $[\alpha]_D^{20}=-227.29°$ (c=0.54 in CHCl$_3$), obtained from cyclosporin 6.11;

6.20 [7'-Desmethyl-7'-phenyl-dihydro-MeBmt]$^1$-[Val]$^2$-Ciclosporin: $[\alpha]_D^{20}=-214°$ (c=1.19 in CHCl$_3$), obtained from cyclosporin 6.8 or 6.9;

6.21 [7'-Desmethyl-7'-ethyl-dihydro-MeBmt]$^1$-Ciclosporin: $[\alpha]_D^{20}=-233°$ (c=1.15 in CHCl$_3$), obtained from cyclosporin 6.33;

As will be apparent, cyclosporins of groups 1a$^2$ and 1a$^3$ and of classes 4, 5 and 6 herein before described, all of which are novel, are structurally related and may, for convenience, readily be subsumed into unified categories, e.g. comprising cyclosporins wherein the residue at the 1-position is a residue of formula XXI

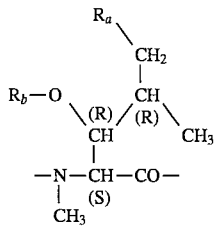

(XXI)

wherein (i) $R_a$ is formyl and $R_b$ has the meanings given for $R_{12}$ in relation to formula XVIII; or (ii) $R_a$ is —y'—x'—$R_c$ whereby —y'—x'—$R_c$ has the meanings given for —y—x—$R_4$, —y—x—$R_6$, or —y—x—$R_6$" in relation to formulae IV, V, XIV and XIX' above and $R_b$ is hydrogen or acyl.

Similarly cyclosporins of groups 1a$^2$ and 1a$^3$ and of classes 4 and 6, all of which are novel and have utility other than as intermediates can be subsumed into unified subcategories, e.g. comprising cyclosporins wherein the residue at the 1-position is a residue of formula XXI as illustrated above, wherein $R_a$ and $R_b$ have the meanings given under (ii) for formula XXI.

Acyl groups as $R_b$ are preferably groups ACYL$^1$ as defined in relation to formulae III and IV, in particular (C$_{1-4}$alkyl)-carbonyl, e.g. acetyl.

Preferred cyclosporins of such categories/sub-categories are those of formula II as illustrated above wherein A is a residue of formula XXI as defined above and B has the meanings given for formula II, X is -Sar- and Y is -Val-.

Various cyclosporins of group 1b) as hereinbefore set forth, e.g. wherein the residue at the 2-position is a residue of formula III' as illustrated above in which ACYL$^3$ is acetyl are known. Thus cyclosporin 1.35 is known and has been described, together with processes for its production in Traber et al., Helv. Chim. Acta, 60, 1247 at seq./(1977). Other cyclosporins of group 1b may be prepared analogously. Cyclosporin 1.36 however is of an entirely novel type. A still further group of cyclosporin in accordance with the present invention accordingly comprises.

Group 1e)

i) A dicarboxylic acid di-ester of a cyclosporin having a β-hydroxy-(L)-α-amino acid residue at the 2-position; in particular:

ii) A dicarboxylic acid di-ester of a cyclosporin having an (L)-threonyl residue at the 2-position; and especially iii) A dicarboxylic acid di-ester of formula XXII

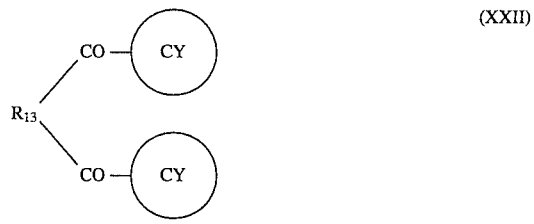

(XXII)

wherein $R_{13}$ is C$_{1-8}$alkylene and each Ⓒʏ represents a residue of formula II as illustrated above wherein A is -MeBmt- or -dihydro-MeBmt- B is an (L) threonyl residue of formula XXIII

(XXIII)

X ia -Sar- and Y is -Val-.

Preferably $R_{13}$ is C$_{1-4}$alkylene.

The present invention also provides a process for the preparation of a cyclosporin of group 1e which process comprises k) reacting a β-O-hemiester of a cyclosporin wherein the residue at the 2-position is a β-hydroxy-(L)-α-amino acid residue, for example a β-O-hemiester of formula XXIV

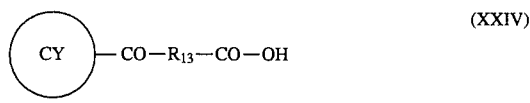

(XXIV)

wherein Ⓒʏ and $R_{13}$ have the meanings given above, or a reactive functional derivative thereof, with a cyclosporin wherein the residue at the 2-position is a β-hydroxy-(L)-α-amino acid residue, for example a cyclosporin of formula II as illustrated above, wherein A is -MeBmt- or -dihydro-MeBmt-, B is -Thr-, X is -Sar- and Y is -Val-.

Reaction may suitably be effected in accordance with the general procedures of the following example G.

EXAMPLE G

Preparation of 1,2-ethanedicarboxylic acid [O-(L)threonyl]$^2$-Ciclosporin di-ester (cyclosporin 1.36)

0.255 g 2-chloro-1-methyl-pyridinium iodide and 0.244 g 4-dimethylamino pyridine are added to 1.318 g [(O-hemisuccinyl)-Thr]2-Ciclosporin in 5 ml absolute CH$_2$Cl$_2$ at 0° C. 1.218 g [Thr]$^2$-Ciclosporin are added, the reaction mixture stirred for 3 hrs. at 0° C., and the temperature allowed to rise to 20° C. with further stirring. The reaction mixture is diluted with $CH_2Cl_2$ and shaken with 10 ml 0.1N NaOH with added ice. The mixture is washed 2× with $H_2O$ and the organic phase dried over $Na_2SO_4$ filtered and evaporated. The raw product is purified chromatographically employing silica gel and hexane/acetone (1:1) as eluant to yield the title compound: $[\alpha]_D^{20}$: −209.4° (c=0.5 in $CHCl_3$).

The [(O-hemisuccinyl)Thr]2-Ciclosporin required as starting material is known—see e.g. International Patent Application No. PCT/EP85/00501. International Patent Publication No. W086/02080, example 5. Other hemiester starting materials suitable for the preparation of cyclosporins of group 1c may be prepared analogously.

Cyclosporins of group 1c as hereinbefore set forth are new and form part of the present invention as novel compounds per se.

The present invention also provides a process for the production of cyclosporins of group 1c, which process comprises.

1) oxidising a cyclosporin wherein in the residue at the 1-position is 3'-hydroxy substituted for example is -McBmt-.

Step 1) above may be performed e.g. by reaction with N-chloro-succinimide/dimethylsulfide at a temperature of e.g. −30° to 10° C., e.g. in accordance with the procedures of example II below.

EXAMPLE II

Preparation of
[3'-desoxy-3'-oxo-McBmt]$^1$-Ciclosporin
(Cyclosporin 1.37)

8.48 ml dimethylsulfide are added at 0° C. to a solution of 12.8 g N-chlorosuccinimide in 400 ml toluene. The mixture is stirred for 5 mins at 0° C., cooled to −12° C. and 9.62 g Ciclosporin in 40 ml toluene are added. The obtained suspension is stirred for 1.5 hrs. at −10° C. and for 1.0 hrs. at −10° to −5° C. 19.4 g triethylamine are added, whereupon a light precipitate forms. The mixture is stirred for 5 hrs. at 0° C., and diluted with 250 ml ethyl ether. 192 ml 1N HCl are added cold and extracted. The organic phase is washed 2× with 500 ml $H_2O$, shaken with 250 ml 10% cold $NaHCO_3$ and washed 2× with 500 ml $H_2O$, 250 ml 10% tartaric acid and again with $H_2O$. The acid and basic aqueous solutions are re-extracted with 2×500 ml ethyl ether. The combined organic phases are dried over $Na_2SO_4$ and evaporated to dryness at 40° C. The residue is purified chromatographically employing 300 g silica gel and saturated aqueous ethyl acetate to yield the title compound: $[\alpha]_D^{20}$=−241.3° (c=0.531 in $CHCl_3$) and −169.5° (c=0.5 in $CH_3OH$). Cyclosporins 1.38 and 1.39 may be prepared analogously:

Physical data:

| | |
|---|---|
| 1.38 | $[\alpha]_D^{20}$ = −255.1° (c = 0.5 in $CHCl_3$) |
| 1.39 | $[\alpha]_D^{20}$ = −235.4° (c = 0.5 in $CHCl_3$) |

Cyclosporins of group 1d as hereinbefore set forth are also new and also form part of the present invention as novel compounds per se.

The present invention also provides a process for the production of cyclosporins of group 1d, which process comprises:

m) oxidising, e.g. selectively oxidising, a cyclosporin wherein the residue at the 2-position is a β-hydroxy-α-amino acid residue, for example an (L)-threonyl residue.

Process step (m) may be carried out entirely analogously to process step (1) above, e.g. in accordance with the general procedures of the following example I.

EXAMPLE I

Preparation of [α-Methylketo-Gly]$^2$-Ciclosporin
(Cyclosporin 1.40)

484 mg dimethylsulfide are added to 868 mg N-chlorosuccinimide in 26 ml toluene at 0° C. After stirring for 10 mins. at 0° C. the suspension is cooled to −30° C. and 1584 mg [Thr]$^2$-ciclosporin in 6.5 ml toluene are added. The reaction mixture is stirred for 1 hr. at 26°–30° C. and 1.81 ml triethylamine are added. Cooling is removed and after a further 5 mins. 25 ml ethyl ether are added. The reaction mixture is poured onto 150 ml ice water/10 ml 1N HCl and stirred and a further 100 ml ethyl ether are added. The organic phase is washed 3× with 150 ml ice water and extracted 2× with ethyl ether. The combined organic phases are dried over $Na_2SO_4$ and concentrated. The residue is dissolved in 10 ml $CH_2Cl_2$, filtered throught Hyflo, diluted with hexane and evaporated to yield the title compound: $[\alpha]_D^{20}$=−229° (c=1.0 in $CHCl_3$) and −184.8° (c=1.0 in $CH_3OH$).

Cyclosporin 1.41 may be prepared analogously: $[\alpha]_D^{20}$= −226.7° (c=1.0 in $CHCl_3$).

Cyclosporins of class 2(i) and of class 2(ii) as hereinbefore set forth are also new and form part of the present invention as novel compounds per se.

In addition the present invention also provides a process for the production of cyclosporins of class 2(i) and 2(ii), which process comprises:

m) for the production of a cyclosporin of class 2(i), reacting a cyclosporin wherein the 3'-carbon atom of the residue at the 1-position is oxo-substituted, e.g. a cyclosporin wherein the residue at the 1-position is -3'-desoxy-3'-oxo-McBmt- with a $C_{1-4}$alkoxyamine, or n) for the production of a cyclosporin of class 2 (ii), cyclising an open-chain peptide comprising the sequence of a cyclosporin comprising an (L)-isoleucyl residue at the 2-position, said open-chain peptide commencing with the residue corresponding to residue 8 of said cyclosporin as N-terminal and terminating with the residue corresponding to residue 7 of said cyclosporin as C-terminal, for example cyclising an open-chain peptide comprising the sequence

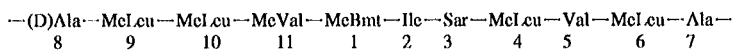

(m) above may be performed, e.g. by reaction with the chosen $C_{1-4}$alkoxyamine, suitably in acid addition salt form, in the presence of a base, such as pyridine, at temperatures of from about −10° to about 80° C., for example in accordance with the general procedures of example J below.

Process step (n) above may be carried out entirely analogously to the general procedures for the total synthesis of cyclosporins, e.g. as described in U.S. Pat. No. 4,554,531 or European patent publication no. 0 098 456. Thus cyclosporin 2.2 is prepared e.g. by substitution of BOC-Ile-OH for BOC-αAbu-OH at step a) of example 1 of said patent/patent publication, and proceeding subsequently in directly analogous fashion to steps (b) through (x) as described in said patent/patent publication.

Cyclosporin 2.2 itself has the following characterising data:

M.P.=151° C./$[\alpha]_D^{20}$=−224° (c=1.0 in $CHCl_3$)

EXAMPLE J

Preparation of
[3'-Desoxy-3'-methoxyimino-MeBmt]$^1$-Ciclosporin
(Cyclosporin 2.1)

600 mg of the product of example H and 835 mg methoxylamine hydrochloride in 2.5 ml ethanol/2.5 ml pyridine are stirred for 14 hrs. at 50° C. under an atmosphere of argon. The pyridine is evaporated off and the remainder filtered. The filtrate is taken up in $CH_2Cl_2$ and washed with brine. The brine is extracted several times with $CH_2Cl_2$ and the combined organic phases again washed with brine, dried and evaporated. The residue is purified chromatographically to yield the title compound: $[\alpha]_D^{20}$=−214° (c=1.09 in $CHCl_3$).

As will be apparent cyclosporins of group 1c and of class 2(i) hereinbefore described, all of which are novel and have utility other than as intermediates can be subsumed into unified sub-categories, e.g. comprising cyclosporins wherein the residue at the 1-position is a residue of formula XXV

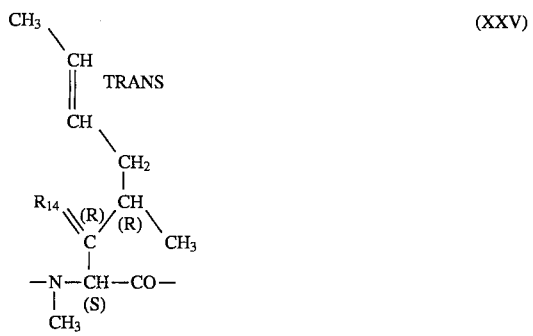

wherein $R_{14}$ is oxygen or a group of formula $R_{15}N=$ wherein $R_{15}$ is $C_{1-4}$alkoxy.

Cyclosporins of class 2(iii) are known. Thus cyclosporins 2.3 to 2.6 are described e.g. in Wenger, Transplantation Proc., XVIII (6) Supp. 5 (December), 213 et seq. (1986). These cyclosporins, as well as other cyclosporins of class 2(iii) may be prepared in accordance with the general procedures for the total synthesis of cyclosporins, e.g. as described in U.S. Pat. No. 4,554,531 and European patent publication no. 0 098 456, e.g. by substitution of H-MeIle-Bzl or H-MeAloIle-Bzl for H-MeVal-Bzl at step (g) of example 1 thereof. Cyclosporins 2.3 to 2.5 have the following characterising data:

| CYCLOSPORIN | m.p. (°C.) | $[\alpha]_D^{20}$ = −; (c = − in $CHCl_3$) |
|---|---|---|
| 2.3 | 162–163 | −178°; 1.0 |
| 2.4 | 144–146 | −221°; 1.0 |
| 2.5 | 146—146 | −225°; 1.0 |
| 2.6 | 148 | −170°; 1.0 |

Cyclosporins 3.1 to 3.5, 3.7 and 3.9 of class 3 are known [see e.g. Traber et al., Helv. Chim. Acta, 65, 1655 et seq. (1982) and 70, 13 et seq. (1987)].

Cyclosporins 3.6, 3.8 and 3.10 are new and are part of the present invention as novel compounds per se. 3.6 and 3.8 may be prepared in a manner entierly analogous to that used for the preparation of other, known dihydrocyclosporins e.g. as hereinbefore described in relation to process step (f).

Cyclosporin 3.10 may be prepared in accordance with the general procedures for the separation of cyclosporin minor metabolites, e.g. as described in Helv. Chim. Acta 65, 1655 et seq. (1982), as a minor metabolite fraction from fermentation broths used in the production of [(D)Ser]$^8$-Ciclosporin (see European patent publication no. 0 056 782), e.g. as described in the following example K.

EXAMPLE K preparation of [MeLeu]$^1$-Ciclosporin (cyclosporin 3.10)

The biomass obtained following cultivation in accordance with example 3 of European patent publication no. 0 056 782 is spun-down in a clarifying separator (Westfalia) and the liquid phase (culture filtrate) extracted 3×, each time with the equivalent amount of ethyl acetate. The ethyl acetate extracts are concentrated under vacuum. The solid phase (mycelium) is treated with methanol and homogenised and solid and liquid phases separated in a clarifying separator. This extraction procedure is repeated 2× using 90% methanol. The methanolic extracts are combined, water is added and the extracts concentrated under vacuum. The remaining aqueous extract concentrate is extracted 3× with the equivalent amount of ethyl acetate and the ethyl acetate extracts concentrated under vaccum. Both raw-extracts (from the culture filtrate and the mycelium) are chromatographed using silica gel (0.040–0.063 mm) and $H_2O$-saturated ethyl acetate. Early eluting fractions contain primarily [Val]$^2$-Ciclosporin (cyclosporin D) followed by fractions containing primarily [MeLeu]$^1$-Ciclosporin (cyclosporin 3.10) and Ciclosporin (cyclosporin A). Peak fractions are chromatographed again using silica gel (0.020∝0.045 mm) and acetone/hexane (1:1) as eluant. [MeLeu]$^1$-Ciclosporin containing fractions are re-chromatographed using LICHROPREP® RP-18 (0.040–0.063 mm) and methanol/$H_2O$ (85:15) as eluant and then silica gel (0.020–0.045 mm) and $H_2O$-saturated ethyl acetate as eluant, to yield the title compound: m.p=142°–148° C., $[\alpha]_D^{20}$=−303° (c=0.54 in $CHCl_3$).

Physical characteristics for cyclosporin 3.6 are: m.p.= 180°–182° C.; $[\alpha]_D^{20}$=−211° (c=0.64 in $CHCl_3$).

As already indicated it has, in accordance with the present invention, now been found that cyclosporins of 1 classes (including cyclosporins of groups 1a$^1$ to 1a$^5$ and 1b to 1e), 2 and 3 and, in particular, individual cyclosporins of these classes hereinbefore specifically named, are capable of increasing or enhancing effectiveness of, or increasing or enhancing sensitivity to, other chemotherapeutic drug therapy, in particular anti-microbial (e.g. anti-bacterial, anti-viral, antifungal or anti-protozoal) chemotherapy and, especially anti-cancer or anti-tumor (e.g. anti-neoplastic or cytostatic) chemotherapy. They are accordingly useful, e.g. as a means of reducing regular chemotherapeutic dosage levels, for example, in the case of anti-neoplastic or cytostatic drug therapy, as a means of decreasing overall drug toxicity and, more especially, as a means of reversing or reducing resistance, including both inherent and acquired resistance, to chemotherapy.

EXAMPLE 1

Utility in restoring sensitivity to anti-neoplastic/cytotoxic, anti-tumor drug substances (in vitro-1)

Cancer cell lines (CCL), e.g. from human small cell carcinoma of the lung, resistant to one or more cancer therapeutic drug substances (CTDS) selected from the group comprising Daunorubicin (DR); Vincristine (VC); Adriamycin (AM); Etoposide (ET); Tenoposide (TE); and Colchicine (CC) are developed in accordance with the methods described by Twentyman et al., Br. J. Cancer, 54, 253 (1986).

Sensitivity of resistant sub-lines (CCL-R) is compared with parental sensitive lines (CCL-S) by assaying inhibition of cell growth during continuous CTDS exposure, e.g. in the case of a DR-resistant line (CCL-DRR) by comparing growth of CCL-DRS and CCL-DRR lines in the presence of DR contained in the growth medium ab-initio. For the purpose, cell proliferation is measured by cell counting using an electronic cell counter, counting being effected close to termination of the exponential growth phase. CCL-R lines are selected for which the $IC_{80}$ (drug concentration e.g. DR concentration, required to reduce final cell number to 20% of that for non-CTDS (e.g. DR) treated controls is <80 X, preferably >100 X, greater than that of parental CCL-S lines.

Sensitivity of selected CCL-R lines to CTDS (e.g. DR) in the presence and absence of test cyclosporin is then performed, employing cell count as a measure of proliferation as described above. For this purpose cells are cultured ab initio in the presence of varying concentrations of both CTDS and test cyclosporin. For screening, concentrations of the latter are chosen which do not themselves cause a significant reduction in proliferation. Appropriate concentrations are established by culturing CCL-S and CCL-R in the presence of varying concentrations of cyclosporin in the absence of CTDS. Cyclosporins are routinely tested at concentrations of from 0.01 to 50, in particular 0.1 to 10, µg/ml, e.g. at concentrations of 0.01, 0.02, 0.05, 0.1, 0.2, 0.5, 1.0, 2.0, 5.0, 10.0 and 50 µg/ml. The ratio of CTDS (e.g. DR) required to inhibit cell proliferation by 50% in the absence of test cyclosporin ($IC_{50}$-CS) compared with that obtained in the presence of test cyclosporin ($IC_{50}$+CS) is taken as a measure of increased sensitivity of the CCL-R line to CTDS which has been induced by the cyclosporin. Stability of the CCL-R line used is ensured by cross checking its sensitivity to CTDS with that previously established.

In the above test model, cyclosporins of classes 1 to 3, in particular specific cyclosporins recited, are effective in increasing sensitivity to CTDS (e.g. DR, VC, AM etc.) at the above indicated concentrations in particular at concentrations of ca. 10 µg/ml, or less.

At higher concentrations, e.g. ca. 50 µg/ml inhibition of proliferation of both CCL-S and CCL-R lines is, in particular instances, occasioned by test cyclosporins in the absence of CTDS, though where this occurs the phenomenon is generally less marked in CCL-R than CCL-S lines. More significantly, test cyclosporins are found to be effective in increasing sensitivity to CTDS in CCL-R lines at concentrations which have no influence on cell proliferation in the absence of CTDS.

Thus in one series of trials employing an AM resistant human small lung cancer cell line, and cyclosporins 2.4, 1.1 and 1.32, established AM sensitisation ratios (AM $IC_{50}$-CS/AM $IC_{50}$+CS) are as follows*:

| CYCLOSPORIN | SENSITISATION RATIO CYCLOSPORIN CONCENTRATION | |
| --- | --- | --- |
| | 50.0 µg/ml | 5.0 µg/ml |
| 2.4 | >30 | >30 |
| 1.1 | .. | >20 |
| 1.35 | 12 | 3.3 |
| NONE | 1.0 | 1.0 |

[*Investigation and data from P.R. Twentyman, MRC Clinical Oncology and Radiotherapeutic Unit, Hills road, Cambridge, England - c.f. Br. J. Cancer, 57, 254-258 (1988)]

EXAMPLE 2

Utility in restoring sensitivity to anti-neoplastic/cytotoxic, anti-tumor drug substances (in vitro-2).

Testing may be performed employing any appropriate drug resistant cell line and control (parental) cell line, generated, e.g. as described by Ling et al., J. Cell. Physiol. 83, 103–116 (1974) and Bech-Hansen et al. J. Cell. Physiol. 88, 23–32 (1976). Particular clones chosen are the multidrug resistant (e.g. colchicine resistant) line CHR (subclone C5S3.2) and the parental, sensitive line AUX B1 (subclone AB1 S11)-c.f. Ling et al. loc. cit. and Juliano et al. Biochim. Biophys. Acta, 455, 152–162 (1976); Carlsen et al. Biochim. Biophys. Acta. 455, 900–912 (1976); Lalande et al., Proc. Natl. Acad. Sci., 78 (1), 363–367 (1981); Kartner et al., Science 221, 1285–1288 (1983); Kartner et al., Nature, 316, 820–823 (1985); Riordan et al., Nature, 316, 817–819 (1985); Van der Blick et al., Mol. Cell. Biol. 6, 1671–1678 (1968); Endicott et al., Mol. Cell Biol., 7, 4075–4081 (1987); Deuchars et al., Mol. Cell. Biol., 7, 718–724 (1987); and Gerlach et al., Nature, 324, 485–489 (1986).

Cell lines are grown in αMEM medium supplemented with (L)-asparagine 0.02 mg/ml, MEM vitamins (IX), penicillin-streptomycin 100 UT/ml, (L)-glutamine 2mM and 10% heat-inactivated fetal calf serum. Assay is performed using 96 well plates. 50 µl colchicine solution are added in the culture medium in triplicates to obtain final concentrations of 30-10-3-1-0.3-0.1-0 µg/ml for the resistant line (RL) and of 0.3-0.1-0.03-0.01-0.003-0.001-0 µg/ml for the sensitive line (SL). Further down-extension of the dose range is performed as necessary, i.e. when test cyclosporin very greatly decreases the $IC_{50}$ response to colchicine.

Test cyclosporins are dissolved at 1 mg/ml in abs. $C_2H_5OH$. Each test cyclosporin is screened routinely at 0.1 and 1.0 µg/ml, with controls being treated with the corresponding $C_2H_5OH$ solvent dilutions. Test cyclosporin or control are added (50 µl) to each well and mixed with colchicine solutions already present. 100 µl cellular suspensions at $4\times10^3$ cells/ml for SL (400 cells/well) and $8\times10^3$ cells/ml for RL are added.

Proliferation is measured by colorimetric assay [Mosman, J. Immunol. Methods, 65, 55–63 (1983)] using 3-(4,5-dimethylthiazol-2-yl)-2,5-diphenyl tetrazolium bromide (MTT). First 100 µl cell-free supernatant is removed, then 10 µl MTT solution at 5 mg/ml in RPMI 1640 medium (Gibco) are added to each plate and the plate incubated for 3 hrs. at 37° C. 100 µl butanol/isopropanol/1N HCl (192:96:12 ml) are then added to each plate and the plates shaken until complete dissolution. Optical density (OD) is read at 540 nm.

Extent of cell growth (measured by MTT-dependent OD) is represented as a function of colchicine concentration, a dose-response curve being constructed for each test cyclosporin, and the colchicine $IC_{50}$ ($CIC_{50}$) (i.e. the concentration of colchicine required to reduce proliferation by 50%) determined.

Increase of colchicine sensitivity induced by each test cyclosporin at both 0.1 and 1.0 µg/ml is determined as:

$$\frac{CIC_{50} \text{ in absence of test cyclosporin}}{CIC_{50} \text{ in presence of test cyclosporin}} = \frac{CIC_{50-}}{CIC_{50+}} = \text{gain in sensitivity}$$

Test cyclosporins may influence colchicine sensitivity in both RL and SL. Relative influence in the two lines may be determined as:

$$\frac{CIC_{50+} \text{ for RL lines}}{CIC_{50+} \text{ for SL lines}} = \frac{CIC_{50} + RL}{CIC_{50} + SL} = \text{relative resistance}$$

Cyclosporins of classes 1 to 3 increase sensitivity of RL to colchicine at concentrations indicated above. Increase of sensitivity of SL is commonly observed at equivalent concentrations though is generally less than for RL. For use in accordance with the present invention, cyclosporins exhibiting higher relative resistance as defined above are generally considered more suitable. In one series of experiments the following gains in sensitivity to colchicine as defined above were, for example recorded for RL and SL.

| CYCLO- | SL | | RL | |
| --- | --- | --- | --- | --- |
| SPORIN | 0.1 µg/ml | 1.0 µg/ml | 0.1 µg/ml | 1.0 µg/ml |
| 1.1 | 4.0 | 8.0 | 1.4 | 30.8 |
| 1.2 | 4.4 | 8.1 | 2.0 | 59.8 |
| 1.3 | 5.3 | 10.7 | 1.8 | 97.9 |
| 1.4 | 6.7 | 11.7 | 1.7 | 97.6 |
| 1.10 | 3.6 | 11.6 | 1.1 | 28.9 |
| 1.11 | 6.3 | 17.6 | 1.1 | 36.7 |
| 1.15 | 4.7 | 12.9 | 1.5 | 38.3 |
| 1.37 | 5.8 | 12.1 | 1.4 | 82.4 |
| 2.2 | 7.9 | 15.1 | 1.5 | 97.3 |
| 2.4 | 4.7 | 15.7 | 1.2 | 34.5 |

EXAMPLE 3

Utility in restoring sensitivity to anti-neoplastic/cytotoxic, anti-tumor drug substances (in vivo)

Ehrlich ascites carcinoma (EA) sub-lines resistant to drug substance DR, VC, AM, ET, TE or CC are developed by sequential transfer of EA cells to subsequent generations of BALB/c host mice in accordance with the methods described by Slater et al., J. Clin. Invest, 70, 1131 (1982). For this purpose drug substance is administered at a dosage of 0.2 to 0.5 mg/kg, i.p. daily over 5 doses, starting 24 hours after inoculation of host mice with 0.2 ml undiluted malignant ascites harvested from pre-terminal animals.

For the test proper, host mice receive resistant EA-R or sensitive (parent) EA-S, EA lines as described above. Mice receiving EA-R are divided into groups receiving:

1. No drug/No cyclosporin
2. Drug-substance therapy/No cyclosporin
3. No drug/Test cyclosporin
4. Drug-substance+Test cyclosporin.

Anti-neoplastic drug substance is administered at dosages employed in generating EA-R lines. Cyclosporin test substance is administered at a total test dosage in the range of from 1 to 80 mg/kg, in particular 5 or 25 or up to 40 mg/kg in 5 divided daily doses, i.p. (in ethanol/olive oil) starting 24 hours after inoculation with EA-R. Mean-survival time in groups 2, 3 and 4 are compared with group 1 as measure of efficacy of applied therapy.

Results obtained show no significant difference in mean-survival time between groups 1, 2 and 3. In group 4, receiving cyclosporin of classes 1 to 3 at dosages as indicated above, substantial increase in survival time (e.g. of the order of 2 to 3 fold or greater) as compared with both groups 1 and 2 is observed.

Equivalent results may be obtained employing cyclosporins of classes 1 to 3 in test models of comparable design, e.g. in vitro, or employing test animals infected with drug-resistant viral strains, anti-biotic (e.g. penicillin) resistant bacterial strains, anti-mycotic resistant fungal strains as well as drug resistant protozoal strains, e.g. Plasmodial strains, for example naturally occurring sub-strains of Plasmodium falciparum exhibiting accquired chemotherapeutic, anti-malarial drug resistance.

Utility of cyclosporins of classes 1 to 3 in accordance with the present invention can also be demonstrated in clinical trials, for example preliminary trials, performed as follows:

CLINICAL TRIAL 1

Subjects (♂ and ♀) are selected from patients diagnosed as exhibiting malignant cancerous growth and to be submitted to anti-neoplastic/cytostatic drug therapy. A detailed report is submitted for each subject entered in the trial detailing case history, disease status, estimated rate of disease progression and estimated prognosis.

Type of anti-neoplastic/cytostatic drug therapy to be applied and estimated dosage rate required in the absence of cyclosporin therapy is determined by the attending physician, having regard to the type and extent of the cancer.

Trial cyclosporin is administered orally at a dosage rate of from 1.0 to 20.0 mg/kg/day or parenterally, e.g. i.v. or i.m., a a dosage rate of from 0.5 to 5.0 mg/kg/day. Where disease status permits, treatment with trial cyclosporin commences at least 1 or 2 days, preferably 10 to 14 days before initiating anti-neoplastic therapy in order to permit build-up to on-going therapeutic dosage levels. In such instances initiating cyclosporin dosages are at the lower end of the above indicated dosage ranges (e.g.: p.o., of the order of from 1.0 to 5.0 mg/kg/day; or parenterally, of the order of from 0.5 to 1.5 mg/kg/day) rising to higher dosage level (e.g. p.o., of the order of from 5.0 to 15.0 or up to 20.0 mg/kg/day or, parenterally, of the order of from 2.0 to 5.0 mg/kg/day), precise regimen being determined by the attending physician having regard to the subject's condition at trial entry. In some cases, it may be required that cyclosporin and anti-neoplastic/cytostatic therapy be initiated and terminated concomitantly, though again with preference for lower initiating cyclosporin dosaging, rising daily to the indicated maximum.

Initiating anti-neoplastic/cytostatic therapy is commenced at ca. ⅓ the estimated dosage rate required in the absence of cyclosporin therapy, precise choice of initiating dosage again being at the discretion of the attending physician. Anti-neoplastic/cytostatic dosaging is increased as required by observed response.

All relevant clinical parameters are monitored throughout the course of the trial, including cyclosporin and anti-neoplastic/cytostatic drug administration rates. Subjects are monitored for control/reduction in tumor growth/occurrence of metastases and possible tumor regression. Reports on disease status and estimated prognosis are submitted at intervals during the course of the trial.

Evaluation of trial results indicate that subjects entered exhibit effective control of or improvement of condition, with restriction of tumor growth or tumor regression and reduction of metastases at anti-neoplastic/cytostatic drug dosage rates below those estimated to be required for equivalent efficacy in the absence of cyclosporin therapy. Reduced incidence of anti-neoplastic/cytostatic drug resistance as compared with reports for groups receiving anti-neoplastic/cytostatic therapy only is recorded, as well as reduced incidence of adverse toxic reaction to administered anti-neoplastic/cytostatic therapy.

CLINICAL TRIAL II

Subjects are chosen from hospitalised or out-patient subjects ($\delta$ and $\varphi$) exhibiting late phase, malignant cancerous growth of whatever type. Subjects selected for trial are patients who have run a full course of anti-neoplastic/cytostatic drug therapy, and who are generally at a late phase of multiple drug treatment and exhibiting renewed onset of tumor growth/metastases etc., i.e. whose cancer is prima facie identifiable as multiple-drug resistant.

A detailed report is submitted for each subject entered in the trial detailing in particular drug therapy applied in the course of the previous 6 to 18 months to date, previous history and current disease status, e.g. estimated rate of disease progression and estimated prognosis.

For the purposes of the trial, entered subjects are maintained on predetermined dose and schedule of anti-neoplastic/cytostatic drug therapy, therapy chosen being that applied at identification of drug resistance and entry into the trial. Anti-neoplastic drug therapy is maintained throughout the trial at the preresistance-determination levels and schedule. The chemotherapy regimen is supplemented by administration of trial cyclosporin, in oral dosage form at a daily dosage rate of from ca. 1 to ca. 20, e.g. ca. 5 to ca. 15, mg/kg/day or administered parenterally, e.g. i.v., at a daily dosage rate of from ca. 0.5 to ca. 7.5, e.g. from ca. 2.0 to ca. 5.0, mg/kg/day. In some patients cyclosporin therapy may commence 1 to up to 14 days before initiating anti-neoplastic therapy and is continued during the entire treatment period. In other cases, it may be required that cyclosporin and anti-neoplastic therapy be initiated and terminated concomitantly.

Subjects are monitored for reduction in tumor growth/occurrence of metastases and possible tumor regression. Reports on disease status and estimated prognosis at the time of examination are submitted at intervals during the course of the trial. In the event that no improvement in condition or restriction of deterioration is reported within an appropriate period, basic anti-neoplastic/cytostatic drug therapy is varied at the discretion of the responsible clinician to alternative, previously applied therapy. All relevant clinical parameters are monitored throughout the course of the trial, including in particular anti-neoplastic/cytostatic drug and cyclosporin serum levels as well as clearance rates.

Evaluation of trial reports indicates that subjects entered exhibit marked improvement in condition, with restriction of tumor growth or tumor regression and decrease in metastases following introduction of cyclosporin therapy, with on-going improvement in disease prognosis.

Cyclosporins of classes 1 to 3 are accordingly useful for the treatment of morbid conditions exhibiting acquired resistance to chemotherapeutic drug treatment, or as adjuvants to chemotherapeutic drug treatment.

The present invention accordingly provides:

1.1 A method of improving or increasing the efficacy of, or of increasing sensitivity to, chemotherapeutic drug therapy; or 1.2 A method of reducing effective chemotherapeutic drug dosage rate;

in a subject in need thereof which method comprises co-administration of a cyclosporin of classes 1 to 3 as hereinbefore defined: or 2.1 A method of treating morbid conditions exhibiting or characterised by resistance, whether accquired, induced or inate, to chemotherapeutic treatment; or 2.2 A method of enhancing or improving chemotherapeutic treatment of morbid conditions exhibiting or characterised by resistance, whether accquired, induced or inate, to said treatment; or 2.3 A method of reversing or reducing resistance, whether accquired, induced or inate, to chemotherapeutic treatment; or 2.4 A method of restoring sensitivity to chemotherapeutic treatment;

in a subject in need thereof, which method comprises administering to said subject an effective amount of a cyclosporin of any one of classes 1 to 3 as hereinbefore defined.

Alternatively the present invention provides:

3. A method of chemotherapeutic treatment in a subject in need thereof which comprises administering an appropriate chemotherapeutically active drug substance together with a cyclosporin of any one of classes 1 to 3 as hereinbefore defined as adjuvant treatment to said drug substance.

The present invention also provides:

4. A cyclosporin of any one of classes 1 to 3 as hereinbefore defined for use in a method as defined under any one of 1.1, 1.2, 2.1, 2.2, 2.3, 2.4 or 3 above; or 5. A cyclosporin of any one of classes 1 to 3 as hereinbefore defined for use in the preparation of a pharmaceutical composition for use in a method as defined under any one of 1.1, 1.2, 2.1, 2.2, 2.3, 2.4 or 3 above.

In that none of the cyclosporins of classes 1 to 3 has previously been proposed or recommended for pharmaceutical or therapeutic use, and in that particular cyclosporins of classes 1 to 3 are indeed novel compounds or cyclosporins of entirely novel type, the present invention also provides:

6. Cyclosporins of classes 1 to 3 as hereinbefore specified, e.g. including individual cyclosporins herein before indicated to be novel as well as cyclosporins of groups 1a$^2$, 1a$^3$, 1a$^4$, 1a$^5$, 1d, 1e and of class 2(i) and 2(iii), for use as pharmaceuticals.

Particular conditions/forms of chemotherapeutic treatment to which the methods of the present invention apply include conditions caused by microbial, e.g. viral, bacterial, fungal or protozoal infection, involving strains resistant to one or more anti-microbial or antibiotic drug substances, e.g. anti-viral, anti-bacterial, anti-fungal or anti-protozoal drug substances.

The methods of the present invention are in particular applicable to the treatment of cancers, e.g. of carcinomas, sarcomas or other tumors or malignant growths, exhibiting induced or accquired resistance to one or more anti-cancer chemotherapeutic drug substances, e.g. anti-neoplastic or cytostatic agents, e.g. anthracyclines or vinca alkaloid drug substances or the specific drug substances daunorubicin, vincristine, adriamycin, etoposide, tenoposide and/or colchicin, e.g. as a means of reducing or reversing tumor growth, occurrence of metastases etc.

Preferred cyclosporins for use in accordance with the present invention are those exhibiting relatively low immunosuppressive activity, e.g. having substantially no immunosuppressive activity at intended dosage levels or which exhibit immunosuppressive activity of an order which is substantially less, e.g. <50%, of that of Ciclosporin. Particular cyclosporins suitable for use in accordance with the methods of the present invention are cyclosporins hereinbefore specifically defined or recited under classes 1 to 3.

Dosages of cyclosporin to be employed in practicing the above methods will of course vary, e.g. depending on the condition to be treated (for example the disease type and the nature of resistance), the particular cyclosporin to be used, the effect desired and the mode of administration.

In general however satisfactory results are obtained on administration orally at dosages of the order from 1 to 20 or up to 50 mg/kg/day, e.g. of the order of from 5 to 10 or up to 15 mg/kg/day administered once or, in divided doses 2 to 4× per day, or on administration parenterally, e.g. intravenously, for example by i.v. drip or infusion, at dosages of the order of from 0.5 to 7.5 up to 10 mg/kg/day, e.g. of the order of from 1.5 or 2.0 up to 5.0 mg/kg/day.

Suitable daily dosages for patients are thus of the order of from 50 to 1,000 up to 2,500 mg p.o., e.g. of the order of from 250 to 500/600 mg p.o., or of the order of from 25.0 to 375.0 up to 500 mg i.v., e.g. of the order of from 75.0 to 100/250 mg i.v.

Alternatively and even preferably, dosaging may be arranged in patient specific manner to provide pre-determined trough blood levels, e.g. as determined by RIA technique. Thus patient dosaging may be adjusted so as to achieve regular on-going trough blood levels as measured by RIA of the order of from 50 or 150 up to 500 or 1000 ng/ml, i.e. analogously to methods of dosaging currently employed for regular Ciclosporin immunosuppressive therapy.

Pharmaceutical compositions suitable for oral administration of cyclosporins of classes 1 to 3 above when practicing the method of the present invention may, for example, be prepared as follows:

| INGREDIENT | | RELATIVE AMOUNT (g) |
|---|---|---|
| i) | LABRAFIL M 1944 CS | 150 |
| ii) | Cyclosporin (e.g. Cyclosporin 1.1, 1.2, 1.3, 1.11 or 1.36) | 25 (dry weight value) |
| iii) | Ethanol (absolute) | 50 |
| iv) | Olive oil | ca. 237 to a |
|  |  | total of ca. 462.0 |

All ingredients are weighed directly into a stirring vessel. Ingredients (i) and (iii) are weighed in first. Ingredient (ii) is then added with continuous stirring until dissolution. Ingredient (iv) is thereafter added with stirring for a further 10 mins. The obtained solution is filtered through a Gelman Preflow Filter (400 μm) at ca. 0.5 to 0.8 bar and filled into 50 ml Rexo bottles. The bottles are sealed with a rubber cork and cap. The entire procedure is carried out under water-free conditions at room temperature with nitrogen gassing (0.25 bar) at all stages. The bottled solution, which is suitable for oral administration, comprises 50 mg cyclosporin (dry weight)/ml. The solution may alternatively be filled into gelatin, e.g. hard or soft gelatin capsules as a means of taste masking. Cyclosporins of classes 4 and 6 and, in particular, individual cyclosporins of these classes hereinbefore specifically named, also exhibit pharmaceutical activity. In particular they exhibit immunosuppressive, anti-inflammatory and anti-parasitic activity as indicated in in vitro and in vivo tests, e.g. as described below. The said cyclosporins also possess activity with respect to experimental allergic encephalomyelitis (EAE) in the rat, again as described below.

EXAMPLE 4

Immunosuppessive activity:

4.1 Local haemolysis in vitro in gel [R. I. Mishell and R. W. Dutton, J. Exp. Medicine, 126, 423–442 (1976)]. Cyclosporins of classes 4 and 6 inhibit haemolysis zones compared with untreated controls at concentrations of from 0.03 to 10.0 μg/ml.

4.2 Lymphocyte stimulation test according to Janossy and Greaves [Clin. Exp. Immunol., 9, 483 (1971) and 10, 525 (1972)]:—cyclosporins of classes 4 and 6 inhibit concanavalin A stimulated DNA-synthesis (inhibition of $H^3$-thymidine incorporation), cell proliferation and blastogenis in mouse-spleen lymphocytes compared with untreated controls at concentrations of from 0.001 to 3.0 μg/ml.

4.3 Mixed lymphocyte reaction [Bach et al., J. Exp. Med. 136, 1430 (1972)]:—the reaction (i.e. proliferation and differentiation) of lymphocytes (mouse (Balb/c) spleen cells]on co-incubation for 5 days, with allogenic spleen cells from irradiated mice (CBA) is measured in the presence and absence of test-substance. Reaction in the absence of test-substance serves as control and is taken as 100%. Reaction in the presence of test-substance is expressed as the % change compared with the 100% control reaction. Inhibition of reaction is observed using cyclosporins of classes 4 and 6 at a concentration of from 0.001 to 3.0 μg/ml.

EXAMPLE 5

Anti-inflammatory activity

Anti-inflammatory activity may be shown in the adjuvant arthritis test in the rat. For this test adjuvant arthritis is induced according to the method of Pearson and Wood, "Arthr. Rheum." 2, 440 (1959). Cyclosporins of classes 4 and 6 are active in this test against developing and established arthritis at doses of from 5 to 30 mg/kg/day p.o.

EXAMPLE 6

Anti-parasitic (anti-malarial) activity

Anti-malaria test according to L. Rane, "Chemotherapy and Drug Resistance in Malaria" ed. W. Peters, Academic Press, New York, 1970. Mice (OFl:male) are infected on day 0 with 0.2 ml of a suspension containing $10^7$ parasitic cells of the species Plasmodium berghei (strain NK 65) administered i.p. Test substance is administered s.c. on day 3, at varying dosages using 5 to 10 mice/dose. The survival time recorded, and the minimum effective dosage (MED) calculated by comparison of survival time with that for untreated controls. For controls survival time=ca. 7 days. The MED is the dosage at which survival time is doubled. Cyclosporins of classes 4 and 6 are effective in this test at dosages of from 10 to 100 mg/kg/day.

EXAMPLE 7

Action on EAE in the rat

1. Action on established EAE

EAE is induced in groups of 8 to 12 otherwise healthy male rats weighing 150 to 200 g in accordance with the techniques described by Borel et al. Agents and Actions 6, 468, (1976). The rats are kept under laboratory conditions and are allowed access to food and water ad libitum. Onset of EAE is observed after 10 to 13 days and is marked by symptoms of paralysis, e.g. in the hind limbs. The test compound is administered to the test animals at a dosage of from 25 to 50 mg/kg p.o. each day for 5 consecutive days following EAE onset. The rats are examined daily for symptoms of the disease and the number of recovered rats as well as the day of recovery noted. Observation is continued for a further 5 to 8 weeks after commencement of treatment to detect any cases of relapse. Again the number of relapsed rats and the day of relapse is recorded.

On administration of cyclosporins of classes 4 and 6 in the dosage range indicated above, a decreased recovery time is noted compared with control groups receiving placebo (olive oil) only.

7.2 Action in preventing the occurrence of EAE

The test is conducted analogously to that described under 4.1 above. In this case, however, the test compound is administered at a dosage of from 25 to 50 mg/kg p.o. each day, starting at the day of sensitisation (induction of EAE) for 14 days. The rats are observed daily for symptoms of paralysis, and the day of onset of EAE in afflicted individuals noted. Observation is continued over a period of months to detect possible delayed onset of EAE.

On administration of Cyclosporins of classes 4 and 6 in the dosage range indicated above prevention of onset of EAE, over the observation period, is observed compared with controls treated with placebo (olive oil) only.

In view of their immunosuppressive activity cyclosporins of classes 4 and 6 are useful for the prophylaxis and treatment of diseases and conditions requiring reduction of the immune response. Thus they may be used to suppress the proliferation of lymphocytes and immunocytes, e.g. in the treatment of auto-immune diseases or in preventing the rejection of organ transplants, e.g. heart, heart-lung, skin, corneal, bone-marrow, pancreatic and kidney transplants.

In view of their anti-inflammatory activity and activity with respect to EAE, cyclosporins of classes 4 and 6 are also useful for the treatment of inflammatory conditions, in particular inflammatory conditions with an aetiology including an autoimmune component, e.g. for the treatment of arthritis (for example rheumatoid arthritis, arthritis chronica progrediente and arthritis deformans) and rheumatic diseases, as well as autoimmune hematological disorder (including e.g. hemolytic anaemia, aplastic anaemia, pure red cell anaemia and idiopathic thrombocytopaenia), systemic lupus erythematosus, polychondritis, sclerodoma, Wegener granulamatosis, dermatomyositis, chronic active hepatitis, myasthenia gravis psoriasis, Steven-Johnson syndrome, idiopathic sprue, autoimmune inflammatory bowel disease (including e.g. ulcerative coliris and Crohn's disease) endocrine opthalmopathy, Grave's disease, sarcoidosis, primary billiary cirrhosis, primary juvenile diabetes (diabetes mellitus type I), uveitis (anterior and posterior), interstitial lung fibrosis, psoriatic arthritis, glomerulonephritis (with and without nephrotic syndrome, e.g. including idiopathic nephrotic syndrome or minimal change nephropathy), and multiple sclerosis.

In view of their anti-parasitic activity, cyclosporins of classes 4 and 6 are also useful for the treatment of parasitic infection. For example coccidiomycosis and schistosomiasis, and, in particular, protozoal infection, especially malaria.

For the above mentioned uses the dose will, of course, vary depending on the cyclosporin chosen, the mode of administration, the particular condition to be treated and the therapy desired. In general, however, satisfactory results are obtained on administration at an oral daily dosage from about 1 to 100, preferably from about 5 to 50, most preferably 10 to 20 mg/kg animal body weight. For the larger mammals e.g. humans, the total daily dosage is in the range of from about 75 to about 2000, preferably from about 200 to about 1000, most preferably from about 300 to about 700 mg. Dosage forms suitable for oral administration comprise from about 20 to about 2000, preferably from about 50 to about 1000, most preferably about 75 to 700 mg cyclosporin admixed with a solid or liquid pharmaceutical diluent or carrier, conveniently administered once or in divided dosages 2 to 4×/day.

As indicated above suitable daily dosage rates will depend, inter al, on the particular cyclosporin chosen, e.g. having regard to its relative potency of action. For preferred cyclosporins of classes 4 and 6 results $IC_{50}$ values (µg/ml)] obtained in one series of experiments in accordance with examples 4 above are as follows:

| CYCLOSPORIN | METHOD OF EXAMPLE | | |
| --- | --- | --- | --- |
| | 4.1 | 4.2 | 4.3 |
| 4.8 | 0.1 | 0.16 | 0.09 |
| 6.4 | 0.03 | <0.008 | <0.008 |
| 6.15 | 0.057 | <0.008 | <0.008 |

The preferred cyclosporin for use in anti-parasitic indications is cyclosporin 4.7. An $ED_{50}$ value obtained for this cyclosporin in the method of example 6 is: ca. 15.0 mg/kg.

In accordance with the foregoing the present invention also provides:

7. A pharmaceutical composition comprising a cyclosporin of class 4 or 6 as hereinbefore defined, together with a pharmaceutically acceptable diluent or carrier therefor;

8. A method of inducing immunosuppression, for the treatment of inflammatory diseases or conditions or for the treatment of parasitic infection, in a subject in need of such treatment which method comprises administering to said subject an effective amount of a cyclosporin of class 4 or 6 as hereinbefore defined; as well as 9. A cyclosporin of class 4 or 6 for use as a pharmaceutical, e.g. for use as an immunosuppressant, as an anti-inflammatory agent or as an anti-parasitic agent.

Particular immunosuppressive, anti-inflammatory and anti-parasitic uses to which the cyclosporins of classes 4 and 6 can be put, include any of those hereinbefore described, e.g. including any of the particular forms of organ transplant, inflammatory disease, autoimmune disease, or parasitic infection listed above.

We claim:

1. A cyclosporin of the formula

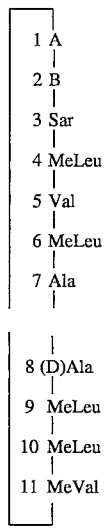

where A is a residue of the formula

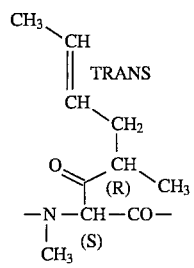

B is -α-Abu-, -Thr-, -Val-, -Nva-, or a residue of the formula

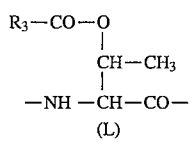

where $R_3$ is $C_{1-4}$alkyl.

2. The compound according to claim 1, which is [3'-desoxy-3'-oxo-MeBmt]$^1$-Ciclosporin.

3. The compound according to claim 1, which is [3'-desoxy-3'oxo-MeBmt]$^1$-[Val]$^2$-Ciclosporin.

4. The compound according to claim 1, which is [3'-desoxy-3'-oxo-MeBmt]$^1$-[Nva]$^2$-Ciclosporin.

5. A pharmaceutical composition comprising a therapeutically effective amount of a cyclosporin according to claim 1 and a pharmaceutically acceptable carrier therefor.

* * * * *